United States Patent
Shibata et al.

(10) Patent No.: US 7,919,564 B2
(45) Date of Patent: Apr. 5, 2011

(54) METHOD FOR MANUFACTURING PARTICULATE WATER-ABSORBING AGENT AND PARTICULATE WATER-ABSORBING AGENT

(75) Inventors: Hirofumi Shibata, Himeji (JP); Kazushi Torii, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 1132 days.

(21) Appl. No.: 11/540,478

(22) Filed: Sep. 28, 2006

(65) Prior Publication Data

US 2007/0078231 A1  Apr. 5, 2007

(30) Foreign Application Priority Data

Sep. 30, 2005  (JP) ................................. 2005-289400

(51) Int. Cl.
*C08F 8/14* (2006.01)
*C08F 8/30* (2006.01)
*C08F 20/06* (2006.01)

(52) U.S. Cl. ................ 525/329.7; 525/329.8; 525/329.9; 525/330.1; 525/375; 525/384; 526/317.1

(58) Field of Classification Search ................ 525/329.7, 525/329.8, 329.9, 330.1
See application file for complete search history.

(56) References Cited

U.S. PATENT DOCUMENTS

| | | |
|---|---|---|
| 4,783,510 A | 11/1988 | Saotome |
| 4,920,202 A | 4/1990 | Irie et al. |
| 4,929,717 A | 5/1990 | Chmelir |
| 5,115,011 A | 5/1992 | Harada et al. |
| 5,210,298 A | 5/1993 | Shimomura et al. |
| 5,229,488 A | 7/1993 | Nagasuna et al. |
| 5,250,640 A | 10/1993 | Irie et al. |
| 5,338,810 A | 8/1994 | Shimimura et al. |
| 5,866,678 A | 2/1999 | Kajikawa et al. |
| 6,207,796 B1 | 3/2001 | Dairoku et al. |
| 6,388,000 B1 | 5/2002 | Irie et al. |
| 6,552,141 B1 | 4/2003 | Chmelir et al. |
| 6,605,673 B1 | 8/2003 | Mertens et al. |
| 6,914,099 B2 | 7/2005 | Kim |
| 6,998,447 B2 | 2/2006 | Irie et al. |
| 7,030,199 B1 | 4/2006 | Chmelir et al. |
| 7,078,458 B2 | 7/2006 | Irie et al. |
| 2006/0036043 A1 | 2/2006 | Nestler et al. |

FOREIGN PATENT DOCUMENTS

| | | |
|---|---|---|
| EP | 0 509 708 A1 | 10/1992 |
| EP | 0505163 B2 | 10/1996 |
| EP | 1 466 928 A1 | 10/2004 |
| EP | 1568385 A1 | 8/2005 |
| JP | 63-207844 A | 8/1988 |
| JP | 3279401 B2 | 2/2002 |
| WO | WO-02/053605 A2 | 7/2002 |
| WO | WO-03/051940 A1 | 6/2003 |
| WO | WO-2004/069915 A1 | 8/2004 |
| WO | WO 2006/062258 A2 * | 6/2006 |
| WO | WO 2006/088115 A1 * | 8/2006 |

* cited by examiner

*Primary Examiner* — Roberto Rabago
(74) *Attorney, Agent, or Firm* — Edwards Angell Palmer & Dodge LLP; David G. Conlin; David A. Tucker

(57) ABSTRACT

The present invention provides a method for manufacturing a particulate water-absorbing agent which has excellent liquid diffusibility and liquid permeability, and whose amount of residual monomers is reduced. The method for manufacturing the particulate water-absorbing agent of the present invention includes a step of surface-crosslinking, in the presence of an organic crosslinking agent, water-absorbing resin particles obtained through at least a step of polymerizing an aqueous solution of unsaturated monomers, and in or after the polymerizing step, a reaction system is mixed with peroxide. Thus, it is possible to obtain the particulate water-absorbing agent which has excellent liquid diffusibility and liquid permeability and whose amount of residual monomers is small, that is, it is possible to obtain the particulate water-absorbing agent which is highly functional and highly safe.

16 Claims, 1 Drawing Sheet

METHOD FOR MANUFACTURING PARTICULATE WATER-ABSORBING AGENT AND PARTICULATE WATER-ABSORBING AGENT

This Nonprovisional application claims priority under 35 U.S.C. §119(a) on Patent Application No. 289400/2005 filed in Japan on Sep. 30, 2005, the entire contents of which are hereby incorporated by reference.

FIELD OF THE INVENTION

The present invention relates to (i) a method for manufacturing a particulate water-absorbing agent preferably used for hygiene materials, such as paper diapers, sanitary napkins and so-called incontinence pads, and (ii) the particulate water-absorbing agent.

BACKGROUND OF THE INVENTION

In the hygiene materials, such as the paper diapers, the sanitary napkins and the incontinence pads, an absorber whose constituent materials are a hydrophilic fiber, such as pulp, and a water-absorbing resin is widely utilized to absorb body fluids.

In recent years, there exists a great need for the hygiene material which has excellent liquid diffusibility and liquid permeability, that is, which is highly functional, and is thin for improving the fit and the water-absorbing performance.

In order to improve the functions of the hygiene material, and at the same time, reduce the thickness thereof, used conventionally is a method for increasing the concentration of the water-absorbing resin in the hygiene material by (i) reducing the amount of hydrophilic fiber having low bulk specific gravity and (ii) increasing the amount of water-absorbing resin having excellent water-absorbing property and high bulk specific gravity. However, this method causes a problem in that influences on skin (skin disorders) become terrible due to, for example, residual monomers contained in the water-absorbing resin. Therefore, in order to improve the functions of the hygiene material, and at the same time, reduce the thickness thereof, it is necessary to simultaneously realize (i) improvements of the liquid diffusibility and liquid permeability of the water-absorbing resin and (ii) reduction in the amount of residual monomers.

So far, disclosed as a method for improving the liquid diffusibility and liquid permeability of the water-absorbing resin are, for example, (i) a method for realizing a product having a water-absorbing speed, a water-absorbing performance and a water-holding property in a balanced manner by impregnating a water-soluble peroxide radical initiator with a base polymer and heating the same to constitute the water-absorbing resin whose interior portion is a soft gel and whose exterior portion is a hard gel (Patent Document 1), (ii) a method for obtaining the water-absorbing resin having excellent holding ability and permeability by coating the water-absorbing resin with a polyol aqueous solution in the presence of an aqueous solution of cation (Patent Document 2), etc.

Moreover, disclosed as a method for reducing the amount of residual monomers are (i) a method for adding, to the water-absorbing resin, a reducing substance which reacts with the residual monomers in the water-absorbing resin, obtaining the water-absorbing resin having a predetermined water content, and heating the water-absorbing resin at a predetermined temperature while the changes of the water content of the water-absorbing resin is maintained in a predetermined range or lower than a predetermined range (Patent Document 3), (ii) a method for adding, in the presence of water, a sulfur atom-containing reducing substance, further adding an oxidizer, and heating the resulting mixture (Patent Document 4), (iii) a method for adding persulfate to crosslinked hydrogel and drying the resulting mixture (Patent Document 5), etc.

However, these conventional technologies cannot simultaneously realize both (i) the improvements of the liquid diffusibility and liquid permeability of the water-absorbing resin and (ii) the reduction in the amount of residual monomers. Thus, when the water-absorbing resin obtained by these conventional technologies is practically used in the hygiene materials such as diapers, physical properties and safety of this water-absorbing resin are insufficient.

That is, although the water-absorbing resin whose amount of residual monomers is small is publicly known, the water-absorbing resin which is highly safe and highly functional when used practically in the hygiene materials such as diapers has not been obtained yet. Therefore, the hygiene material which is highly safe and highly functional has not been obtained yet.

Conventionally, the water-absorbing resin whose amount of residual monomers is small is disclosed in, for example, U.S. Pat. Nos. 4,929,717, 4,90,202, 5,116,011, 5,250,640, 5,210,298, 5,338,810, 5,229,488, 5,866,678 (Patent Document 3), U.S. Pat. Nos. 6,207,796, 6,552,141 and 7,030,199, and European Patent No. 0505163. Generally, a step of reducing the amount of residual monomers becomes a cause of an increase in cost. In addition, this step of reducing the amount of residual monomers tends to deteriorate the physical properties of the water-absorbing resin. Thus, it is difficult to simultaneously obtain both the improvements of the physical properties of the water-absorbing resin and the reduction in the amount of residual monomers.

Moreover, among methods for reducing the amount of residual monomers, widely known is a method (for example, a method disclosed in Patent Document 3) for adding, as an additive, to the water-absorbing resin a water-soluble compound (for example, sulfite or bisulfite) which reacts with the residual monomers. However, since this additive is usually used in the form of an aqueous solution, there are problems in that (i) a drying treatment is required and (ii) the water content of the water-absorbing resin increases (the solid content decreases) as the amount of residual monomers decreases.

Further, in recent years, there is a demand for the water-absorbing resin having higher physical properties. That is, in addition to the improvements of a centrifuge retention capacity (CRC) and an absorbency against pressure (AAP), there is even a demand that, for example, the liquid permeability under load such as a saline flow conductivity (SFC, see U.S. Pat. No. 5,669,894, U.S. Pat. No. 6,849,665B1, U.S. Pat. No. 6,620,889B1, U.S. Pat. No. 6,605,673B1, etc.) is improved several times to several tens of times the conventional value (the liquid permeability under load is conventionally 1 ($\times 10^{-7} \cdot cm^3 \cdot s \cdot g^{-1}$) to 10 ($\times 10^{-7} \cdot cm^3 \cdot s \cdot g^{-1}$)).

Means for improving these physical properties (especially, SFC) is to increase a surface-crosslinking density of the water-absorbing resin. However, since long surface-crosslinking or high-temperature surface-crosslinking accelerates thermal deposition of impurities (acrylic acid oligomer (U.S. Patent No. 2006-0036043) and β-hydroxypropionic acid (U.S. Pat. Nos. 6,388,000, 6,998,447 and 7,078,458)) of raw acrylic acid to acrylic acid, the residual monomers (residual acrylic acid) increase. Thus, there is a problem in that the residual monomers (residual acrylic acid) increase by improving the physical properties (especially, SFC).

That is, it has conventionally been difficult to simultaneously obtain both high physical properties (especially, high SFC) and the reduction in the amount of residual monomers. Moreover, according to methods, disclosed in Patent Documents 3 to 5, for reducing the residual monomers, there is a problem in that the water content of the water-absorbing resin increases as the amount of residual monomers decreases.

Moreover, as the surface-crosslinking method other than the heating, known is a method for (i) mixing the water-absorbing resin with a water-soluble radical polymerization initiator and (ii) irradiating the mixture with an active energy ray (Patent Document 6). However, this method is not preferable since the amount of the water-soluble radical polymerization initiator used is very large, it is not economical, and the obtained water-absorbing resin may become brown or yellow in color.

Moreover, in this method, the amount of water used together with the water-soluble radical polymerization initiator is also very large. Further, since this method does not require heating, the water content of the obtained water-absorbing resin is kept high, but as a result, the amount of absorption per unit weight of the obtained water-absorbing resin deteriorates. Therefore, this water-absorbing resin may not be suitable for the hygienic material which contains a large amount of the water-absorbing resin. Moreover, the other properties (such as SFC) of this water-absorbing resin are also insufficient.

Moreover, as described above, although the water-absorbing resin whose amount of residual monomers is small is conventionally known, the amount of residual monomers has been evaluated by (i) dispersing the water-absorbing resin in a large excess of water (the amount of water is several hundreds of times to several thousands of times the amount of the water-absorbing resin), (ii) extracting the residual monomers, and (iii) measuring the amount of residual monomers contained in the entire water-absorbing resin. However, since the water-absorbing resin that is a form (practical use form) used practically in the hygiene materials such as diapers is not dispersed in a large excess of water but is in a dry state in which liquid urine does not exist practically, it is found that the amount of residual monomers measured by the above method using a large excess of water does not correlate with the amount of residual monomers contained in the water-absorbing resin of practical use form.

That is, it is found that (i) the amount of residual monomers measured by a conventional method does not express the amount of residual monomers exuding in the hygiene materials such as diapers and (ii) it cannot be an index of diaper rash or safety. Especially, in order to increase the amount of absorption and reduce the thickness, the amount of water-absorbing resin used in the hygiene materials such as diapers is increasing in recent years. The amount of water-absorbing resin used in the hygiene material is 50 weight % or more of an absorber layer, and in some hygiene materials, it is 70 weight % or more. Therefore, it is important to improve both the physical properties and reduce the amount of residual monomers.

Here, in addition to the conventional problems in that (i) the reduction in the amount of residual monomers leads to an increase in cost, (ii) it is difficult to simultaneously realize both the reduction in the water content and the reduction in the amount of residual monomers, (iii) it is difficult to simultaneously realize both high physical properties (especially, high SFC) and the reduction in the amount of residual monomers, etc., the present inventors has tackled a new task of providing the water-absorbing resin of practical use form whose amount of residual monomers is small.

As a result, it is found that a surface residual monomer ratio that is a new parameter truly expresses the amount of residual monomers in the water-absorbing resin of practical use form in the hygiene materials such as diapers. Moreover, the present inventors found that by (i) controlling the surface residual monomer ratio to be a value in a certain range or less than a certain range, and (ii) using the water-absorbing resin whose physical properties (especially, SFC) (the improvements of these physical properties (especially, SFC) cannot be realized simultaneously with the reduction in the amount of residual monomer) are improved to a certain level or higher, it is possible to obtain the hygiene material which can simultaneously realize both high physical properties and the reduction in the amount of residual monomers. Thus, the present inventors have completed a new particulate water-absorbing agent of the present invention.

Patent Document 1
U.S. Pat. No. 4,783,510
Patent Document 2
U.S. Pat. No. 6,605,673 B1
Patent Document 3
U.S. Pat. No. 5,866,678
Patent Document 4
Japanese Patent No. 3279401
Patent Document 5
U.S. Pat. No. 6,914,099 B2
Patent Document 6
WO2006/062258A2

SUMMARY OF THE INVENTION

The present invention was made to solve the above problems, and an object of the present invention is to provide (i) a method for manufacturing a particulate water-absorbing agent which has excellent liquid diffusibility and liquid permeability and whose amount of residual monomers is reduced, and (ii) the particulate water-absorbing agent.

As a result of diligent study to solve the above problems, the present inventor found (I) that both (i) the improvements of the liquid diffusibility and liquid permeability of the particulate water-absorbing agent and (ii) the reduction in the amount of residual monomers are simultaneously realized by carrying out a crosslinking reaction using peroxide and an organic crosslinking agent in a step of manufacturing the particulate water-absorbing agent, and especially, (II) that the greatest effect can be obtained by adding, to the water-absorbing resin particles, an aqueous solution containing peroxide and the organic crosslinking agent in a surface-crosslinking step. In this way, the present inventor has achieved the present invention.

In order to achieve the above object, a method for manufacturing the particulate water-absorbing agent of the present invention includes the step of surface-crosslinking, in the presence of an organic crosslinking agent which can react with a carboxyl group, water-absorbing resin particles obtained through at least a step of polymerizing an aqueous solution of unsaturated monomers, and in the surface-crosslinking step, a reaction system of the method is not irradiated with an active energy ray having a wavelength that is equal to or less than a wavelength of an ultraviolet ray, and the surface-crosslinking step is carried out in the presence of peroxide, the organic crosslinking agent and water.

According to the above, the peroxide added to the reaction system in the polymerizing step or after the polymerizing step but before the end of the surface-crosslinking step, or the peroxide added to the reaction system in the polymerizing step and remaining in the reaction system after the end of the polymerizing step causes, together with the organic crosslinking agent, the crosslinking reaction in the vicinity of the surface of the water-absorbing resin particle. Therefore, it is believed that a surface crosslinking layer stronger than a conventional one may be formed and gel strength may be improved. As a result, it is believed that the liquid diffusibility and liquid permeability of the water-absorbing resin may be improved.

Moreover, it is possible to reduce the amount of residual monomers by causing peroxide radical, generated by heating the peroxide, and the residual monomers in the water-absorbing resin to react with each other. It is found that in a step of drying a particulate hydrated gel in a method for manufacturing the water-absorbing resin, especially many residual monomers exist in the vicinity of the surface of the dried particulate water-absorbing resin because, for example, (i) the residual monomers move to the vicinity of the surface of the particle due to the movement, by heat, of the moisture to outside the particle, or (ii) the reactivity between the residual monomers and residual peroxide reduces since the drying speed of the surface of the hydrated gel is high and the water content easily reduces.

Therefore, it is believed that a method using the peroxide and the organic crosslinking agent in the surface-crosslinking step can especially obtain a highest effect of reducing the amount of residual monomers. As a result, it is believed that it may be possible to provide the particulate water-absorbing agent which is highly functional and highly safe.

In order to achieve the above object, a particulate water-absorbing agent of the present invention is obtained by surface-crosslinking, by an organic crosslinking agent which can react with a carboxyl group, water-absorbing resin particles, 70 mole % to 100 mole % of which are, as a repeat unit, monomers that are one or both of acrylic acid and its salt, and the particulate water-absorbing agent satisfies (i) to (vi) below:

(i) a surface residual monomer ratio calculated by Formula 1 below being more than 0% but not more than 5%;

Surface Residual Monomer Ratio (%)=Amount of Surface Residual Monomers (ppm)/Amount of Residual Monomers (ppm)×100    Formula 1

(ii) a saline flow conductivity (SFC) being 40 ($\times 10^{-7} \cdot cm^3 \cdot s \cdot g^{-1}$) or more; and (iii) a water content being less than 5%.

This particulate water-absorbing agent is a highly. functional particulate water-absorbing agent which (i) has physical properties correlated to a practical use in the hygienic materials such as diapers, especially to a practical use in high density diapers containing a large amount of water-absorbing resin, and (ii) has excellent liquid diffusibility, excellent liquid permeability and a reduced amount of residual monomers.

Additional objects, features, and strengths of the present invention will be made clear by the description below. Further, the advantages of the present invention will be evident from the following explanation in reference to the drawings.

DESCRIPTION OF THE EMBODIMENTS

Figure 1:
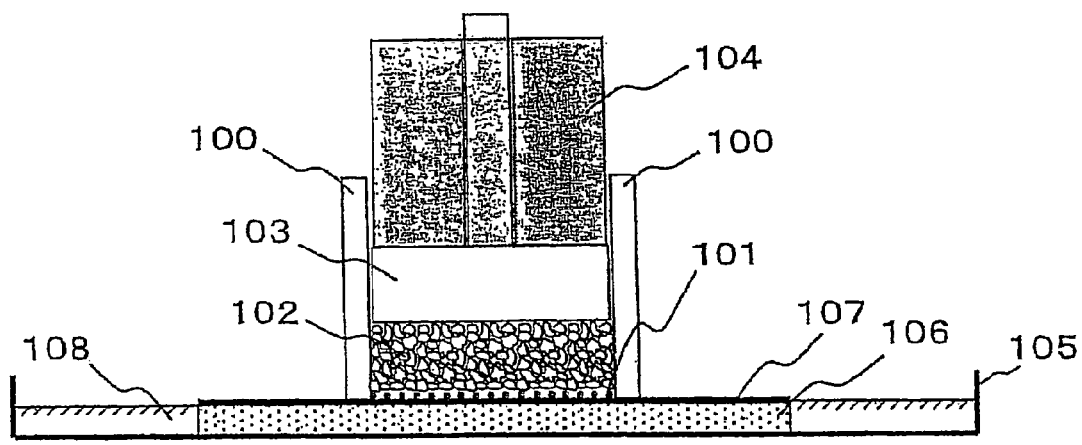
FIG. 1 is a schematic diagram showing an apparatus for measuring the AAP.

The following will explain the present invention in detail. However, the present invention is not limited to the following explanation. Other than the following exemplification, the present invention may be applied in many variations within the spirit of the present invention.

[Method for Manufacturing Particulate Water-Absorbing Agent]

In one embodiment, a method for manufacturing a particulate water-absorbing agent of the present invention includes a step of surface-crosslinking, in the presence of an organic crosslinking agent, water-absorbing resin particles obtained through at least a step of polymerizing an aqueous solution of unsaturated monomers, and in or after the polymerizing step, a reaction system is mixed with peroxide.

In the present specification, "the water-absorbing resin particle" is a particle of (i) a hydrated gel crosslinked polymer or (ii) a dry substance of the hydrated gel crosslinked polymer, and is in the shape of a particle (spherical shape, indeterminate shape, or agglomerated substance thereof) having the absorbency of at least ten times or more in the case of a physiological saline solution (0.90 mass % NaCl aqueous solution). The water soluble element of the water-absorbing resin particle is preferably 50% or less, and more preferably 25% or less, and the water-absorbing resin particle is water-insoluble.

Moreover, in the present specification, "the water-absorbing resin" is a water-swelling water-insoluble polymer obtained by introducing a crosslinked structure to a hydrated gel crosslinked polymer.

Note that "water insolubility (water-insoluble)" is a practical water insolubility (practically water-insoluble) and means that the water-soluble element in the water-absorbing resin is necessarily from 0 weight % to 50 weight %, preferably from 0 weight % to 25 weight %, more preferably from 0 weight % to 15 weight %, and further preferably from o weight % to 10 weight %.

In the present invention, the water-absorbing resin particle may be simply termed "the water-absorbing resin". In addition, in the present specification, "the particulate water-absorbing agent" is the water-absorbing resin particle subjected to the surface crosslinking.

<Polymerizing Step>

The polymerizing step is a step of polymerizing an aqueous solution of unsaturated monomers to produce a hydrated gel crosslinked polymer, and is the first step in a process of manufacturing the particulate water-absorbing agent. As a polymerization method, bulk polymerization, reversed-phase suspension polymerization, or precipitation polymerization can be carried out. However, in light of performances and the ease of control of the polymerization, it is preferable to carry out the reversed-phase suspension polymerization or aqueous polymerization using the aqueous solution of unsaturated monomers, and it is especially preferable to carry out the aqueous polymerization.

The concentration of monomers in the aqueous solution is preferably from 20 mass % to the saturated concentration, further preferably from 30 mass % to 70 mass %, and especially preferably from 35 mass % to 60 mass %.

This polymerization method is disclosed, for example, in U.S. Pat. Nos. 4,625,001, 4,769,427, 4,873,299, 4,093,776, 4,367,323, 4,446,261, 4,683,274, 4,690,996, 4,721,647, 4,738,867 and 4,748,076, European Patent No. 1178059, etc.

The unsaturated monomer is a monomer having water solubility, and preferably contains acrylic acid and/or its salt as a main component (the amount of acrylic acid and/or its salt in the entire monomers is from 50 mole % to 100 mole %, preferably from 70 mole % to 100 mole %, further preferably from 90 mole % to 100 mole %). It is preferable to use this monomer because the water-absorbing performance and safety of the obtained hydrated gel improve further. Note that the monomer having the water solubility is a monomer, 1 g (or 10 g) or more of which dissolves in 100 g of water at room temperature.

Here, acrylic acid and/or its salt is acrylic acid and/or water-soluble salt of acrylic acid. Moreover, water-soluble salt of acrylic acid is alkali metal salt of acrylic acid, alkali earth metal salt of acrylic acid, ammonium salt of acrylic acid, hydroxy ammonium salt of acrylic acid, amine salt of acrylic acid, or alkylamine salt of acrylic acid, whose neutralization ratio is in a range from 30 mole % to 100 mole %, preferably in a range from 50 mole % to 99 mole %. These acrylic acid salt based monomers may be used alone or in combination of two or more thereof.

The monomer containing acrylic acid and/or its salt as the main component may be copolymerized with the other monomer according to need. Specific examples of the other monomer are (i) anionic unsaturated monomer and its salt, such as methacrylic acid, maleic acid, vinyl sulfonic acid, styrene sulfonic acid, 2-(meth)acrylamide-2-methylpropanesulfonic acid, 2-(meth)acryloyloxy ethanesulfonic acid and 2-(meth) acryloyloxy propanesulfonic acid, (ii) nonionic hydrophilic group-containing unsaturated monomer, such as acrylamide, methacrylamide, N-ethyl(meth)acrylamide, N-n-propyl (meth)acrylamide, N-isopropyl(meth)acrylamide, N,N-dimethyl(meth)acrylamide, 2-hydroxyethyl(meth)acrylate, 2-hydroxypropyl(meth)acrylate, methoxypolyethyleneglycol(meth)acrylate, polyethylene glycol mono(meth)acrylate, vinylpyridine, N-vinylpyrrolidone, N-acryloyl piperidine, N-acryloyl pyrrolidine and N-vinylacetamide, (iii) cationic unsaturated monomer, such as N,N-dimethylaminoethyl (meth)acrylate, N,N-diethylaminoethyl(meth)acrylate, N,N-dimethylaminopropyl(meth)acrylate, N,N-dimethylaminopropyl(meth)acrylamide and their quaternary salts, etc. The amount of the above-described other monomers (not the monomers containing acrylic acid and/or its salt) is preferably from 0 mole % to 30 mole % of the entire monomers, and more preferably from 0 mole % to 10 mole %.

In the above polymerizing step, a monomer composition containing the unsaturated monomer as the main component is polymerized preferably in the presence of a crosslinking agent. In this way, the hydrated gel crosslinked polymer can be obtained. The hydrated gel crosslinked polymer may be a self crosslinking type which does not require the crosslinking agent. However, it is preferable that the hydrated gel crosslinked polymer be a hydrated gel crosslinked polymer obtained by being copolymerized or reacted with a crosslinking agent having, in one molecule, two or more polymerizable unsaturated groups, or two or more reactive groups.

Further, the monomer composition may contain the other hydrophobic unsaturated monomer which can be copolymerized with the above unsaturated monomer, as long as the hydrophilic property of the obtained hydrated gel crosslinked polymer is not hindered. Specific examples of the copolymerizable monomer are (i) (meth)acrylic esters, such as methyl (meth)acrylate, ethyl(meth)acrylate and butyl(meth)acrylate, and (ii) hydrophobic monomers not containing an acid group, a hydroxyl group or an amino group, such as vinyl acetate and vinyl propionate. These copolymerizable monomers may be used alone or in combination of two or more thereof.

Moreover, specific examples of the crosslinking agent (another name: internal crosslinking agent) used when polymerizing the monomer composition are N,N'-methylenebis (meth)acrylamide, (poly)ethylene glycol di(meth)acrylate, (poly)propylene glycol di(meth)acrylate, (ethylene oxide modified) trimethylolpropane tri(meth)acrylate, trimethylolpropane di(meth)acrylate, glycerin tri(meth)acrylate, (ethylene oxide modified) glycerin acrylate methacrylate, pentaerythritol tetra(meth)acrylate, dipentaerythritol hexa(meth) acrylate, N,N-diallyl acrylamide, triallyl cyanurate, triallyl isocyanurate, triallyl phosphate, triallyl amine, diallyl oxyacetate, bis(N-vinyl carboxylic amide), (ethylene oxide modified) tetraallyloxy ethane, poly(meth)allyloxy alkane, (poly) ethylene glycol diglycidyl ether, glycerol diglycidyl ether, ethylene glycol, polyethylene glycol, propylene glycol, glycerin, pentaerythritol, ethylene diamine, polyethyleneimine, glycidyl(meth)acrylate, etc.

These internal crosslinking agents may be used alone or in combination of two or more thereof. However, in light of the water-absorbing property, or other properties of the obtained water-absorbing resin particles, it is preferable to necessarily use, as the internal crosslinking agent, a compound containing two or more polymerizable unsaturated groups. The amount of the compound used is preferably from 0.005 mole % to 3 mole % of the entire monomers, and more preferably from 0.01 mole % to 1.5 mole %.

When carrying out the polymerization, (i) a hydrophilic polymer, such as starch-cellulose, derivative of starch-cellulose, polyvinyl alcohol, polyacrylic acid (salt) or crosslinked polyacrylic acid (salt), or (ii) a chain transfer agent, such as hypophosphorous acid (salt), may be added.

The amount of the hydrophilic polymer used is preferably from 0 mass part to 50 mass parts of the entire monomers, further preferably from 0 mass part to 30. mass parts, and most preferably from 0 mass part to 10 mass parts.

The amount of the chain transfer agent used is preferably from 0.001 mole % to 1 mole % of the entire monomers, further preferably from 0.005 mole % to 0.5 mole %, and most preferably from 0.01 mole % to 0.3 mole %.

When starting the polymerization, it is possible to use, for example, a polymerization initiator or an active energy ray, such as a radiation ray, an electron ray, an ultraviolet ray or an electromagnetic ray. The polymerization initiator is not especially limited, but may be a thermally decomposable initiator or an optically decomposable initiator.

Examples of the thermally decomposable initiator are (i) persulfate, such as sodium persulfate, potassium persulfate and ammonium persulfate, (ii) peroxide, such as hydrogen peroxide, t-butyl peroxide and methyl ethyl ketone peroxide, and (iii) an azo compound, such as an azo nitryl compound, an azo amidine compound, a cyclic azo amidine compound, an azo amide compound, an alkyl azo compound, 2,2'-azobis(2-amidino propane)dihydrochloride and 2,2'-azobis[2-(2-imidazoline-2-yl)propane]dihydrochloride.

Examples of the optically decomposable initiator are a benzoin derivative, a benzil derivative, an acetophenone derivative, a benzophenone derivative, an azo compound, etc. These polymerization initiators may be used alone or in combination thereof. Moreover, in the case of using the peroxide as the polymerization initiator, an oxidation-reduction polymerization (redox polymerization) may be carried out using a reducing agent, such as subsulfate, bisulfite or L-ascorbic acid.

The amount of the polymerization initiator used is preferably from 0.001 mole % to 2 mole % of the entire monomers, and more preferably from 0.01 mole % to 0.5 mole %. Through the polymerizing step described above, the hydrated gel crosslinked polymer can be obtained. The solid content (water content) of the hydrated gel polymer is accordingly determined depending on the concentration of the aqueous solution, evaporation of water during the polymerization, etc.

A method for manufacturing the particulate water-absorbing agent of the present invention may include a gel pulverizing step of pulverizing the aggregated hydrated gel crosslinked polymer, obtained through the polymerizing step, to obtain particles of the hydrated gel crosslinked polymer. By realizing the particulate hydrated gel, the surface area of the gel increases. Therefore, it is possible to smoothly carry out a drying step explained below. The above pulverizing may be carried out with various cutting means, such as a roller cutter, a guillotine cutter, a slicer, a roll cutter, a shredder, a pair of scissors or a combination thereof, and is not especially limited.

Thus, the above water-absorbing resin particles may be the particles of the hydrated gel crosslinked polymer. Moreover, the above water-absorbing resin particles may be particles obtained through the drying step (will be described late) of drying the hydrated gel crosslinked polymer, and then the pulverizing step, a classifying step, and/or the like.

<Drying Step>

The drying step is a step of drying the hydrated gel crosslinked polymer obtained through the polymerizing step, and is preferably a step of drying the particulate hydrated gel obtained through the gel pulverizing step. Note that the drying means that the solid content is increased by 10% or more or that the water content become 25% or less.

A method for the drying is not especially limited, and it is possible to use, for example, one, or two or more of a band dryer, an agitation dryer and a fluidized bed dryer, that is, it is possible to preferably use conventional drying methods. The water content (defined by a weight reduction at 180° C. for 3 hours) after the drying is controlled to be preferably from 0 mass % to 25 mass %, further preferably from 1 mass % to 15 mass %, and more preferably from 2 mass % to 10 mass %.

A drying temperature or drying time for the hydrated gel crosslinked polymer is not especially limited, but the drying temperature is usually from 70° C. to 250° C., preferably from 150° C. to 230° C., and more preferably from 160° C. to 180° C. Note that the drying temperature is the temperature of a heat medium. In the case of carrying out the drying at less than 70° C., it requires a long time, so that it is not preferable in light of productivity. Moreover, in the case of carrying out the drying at more than 250° C., the resin deteriorates. When the drying temperature cannot be defined by the temperature of the heat medium (for example, in the case of carrying out the drying using microwave), it is defined by the temperature of a material.

The drying time is set accordingly, and is usually from 1 minute to 5 hours, and preferably about from 10 minutes to 2 hours.

Moreover, a method for manufacturing the particulate water-absorbing agent of the present invention preferably includes the pulverizing step and classifying step carried out after the drying step. The pulverizing step is a step of pulverizing the dried hydrated gel crosslinked polymer with a pulverizer to obtain particles of the dried hydrated gel crosslinked polymer. Examples of the pulverizer used in the pulverizing step are a roller mill, a knife mill, a hammer mill, a pin mill, a jet mill, etc. Moreover, it is preferable that the pulverizer have means for heating an inner wall surface thereof.

The classifying step is a step of consecutively classifying the particles obtained in the pulverizing step. The classifying step is preferably carried out by sieve classification (a metal sieve, made of stainless steel), but is not especially limited to this. Preferably, for desired physical properties and particle size, it is preferable that (i) a plurality of sieves be simultaneously used in the classifying step, and (ii) the classifying step is carried out before a surface-crosslinking step (will be described later) or is carried out twice, that is, before and after the surface-crosslinking step. It is preferable that the sieves be heated or kept warm in the classifying step.

<Surface Crosslinking Step>

The surface-crosslinking step is a step of surface-crosslinking the water-absorbing resin particles. In one preferable example of a manufacturing method of the present invention, an important feature is that the surface crosslinking is carried out using the peroxide and the organic crosslinking agent. As a result, it is possible to obtain the particulate water-absorbing agent which has excellent liquid diffusibility and liquid permeability and whose amount of residual monomers is small. That is, the surface-crosslinking step is an essential step. Note that "the surface crosslinking" means that a functional group (especially, a carboxyl group) on the surface of the water-absorbing resin particle and a compound (the organic crosslinking agent) which can react with the functional group are caused to be reacted with each other.

Here, the centrifuge retention capacity (CRC) of the water-absorbing resin subjected to the surface-crosslinking is decreased by at least 1 g/g or less from the CRC of the water-absorbing resin not subjected to the surface-crosslinking, and the absorbency against pressure (AAP) improves by at least 10 g/g or more. The CRC and the AAP will be described later. Moreover, specifically, in the case of surface-crosslinking the water-absorbing resin obtained by polymerizing monomer having carboxyl groups, the carboxyl groups remained after the surface-crosslinking are labeled by a fluorine compound (2,2,2-trifluoroethanol), and the ratio of fluorine/carbon atom is measured (ESCA measurement). Thus, it is possible to obtain the percentage of reaction of the organic crosslinking agent and the carboxyl group.

Note that the surface-crosslinking step in the present invention is a series of steps of an addition of the surface crosslinking agent, its crosslinking reaction (usually, heat treatment), and, according to need, its stopping (cooling).

Moreover, a technology of polymerizing monomers on a particle surface to form a surface coating is not included in the surface crosslinking defined in the present application.

(1. Organic Crosslinking Agent)

The organic crosslinking agent is not especially limited as long as it can react with an acid group. The organic crosslinking agent may be a dehydration reactive crosslinking agent, an epoxy compound, a polyvalent isocyanate compound, a polyvalent oxazoline compound, or the like. However, it is preferable to use the dehydration reactive crbsslinking agent because it is possible to carry out the surface crosslinking more safely and quickly.

Moreover, in the present specification, the term "dehydration reactive" means that the crosslinking is carried out by a dehydration reaction between the functional group (especially, the functional group in the vicinity of the surface) of the water-absorbing resin and the crosslinking agent, preferably by a dehydration esterification and/or a dehydration amidation, and further preferably by the dehydration esterification. Examples of the functional group are an amino group, a hydroxyl group, etc. However, the functional group is preferably a carboxyl group.

Specifically, when the water-absorbing resin contains the carboxyl group, examples of the dehydration reactive crosslinking agent are (i) a crosslinking agent containing the hydroxyl group, such as polyhydric alcohol, (ii) a crosslinking agent containing the amino group, such as polyvalent amine, and (iii) a cyclic crosslinking agent, such as alkylene carbonate, a mono-, di-, or polyoxazolidinone compound or an oxetane compound (for example, 3-methyl-3-oxetane methanol). Note that in the case of the cyclic crosslinking agent, a hydroxyl group or an amino group is generated by a ring-opening reaction of the cyclic crosslinking agent, and the hydroxyl group or the amino group carries out the crosslinking reaction. These dehydration reactive crosslinking agents may be used alone or in combination of two or more thereof.

Specifically, the dehydration reactive crosslinking agent which can be used in the present invention is not limited as long as it can react with the acid group of the water-absorbing resin, and examples of the dehydration reactive crosslinking agent are crosslinking agents (the surface crosslinking agents) that are usually used in this application.

Examples of the dehydration reactive crosslinking agent are one, or two or more of (i) polyhydric alcohol compounds, such as ethylene glycol, diethylene glycol, propylene glycol, triethylene glycol, tetraethylene glycol, polyethylene glycol, 1,3-propanediol, dipropylene glycol, 2,2,4-trimethyl-1,3-pentanediol, polypropylene glycol, glycerin, polyglycerin, 2-butene-1,4-diol, 1,3-butanediol, 1,4-butanediol, 1,5-pentanediol, 1,6-hexanediol, 1,2-cyclohexanedimethanol, 1,2-cyclohexanol, trimethylolpropane, diethanolamine, triethanolamine, polyoxypropylene, an oxyethylene-oxypropylene block copolymer, pentaerythritol and sorbitol, (ii) polyvalent amine compounds; such as ethylenediamine, triethylenetetramine, tetraethylenepentamine, pentaethylenehexamine, polyamido polyamine, polyallylamine and polyethyleneimine, their inorganic salts or organic salts (for example, azetidinium salt) and condensates of those polyvalent amines and haloepoxy compounds, (iii) alkylene carbonate compounds, such as 1,3-dioxolane-2-one, 4-methyl-1,3-dioxolane-2-one, 4,5-dimethyl-1,3-dioxolane-2-one, 4,4-dimethyl-1,3-dioxolane-2-one, 4-ethyl-1,3-dioxolane-2-one, 4-hydroxymethyl-1,3-dioxolane-2-one, 1,3-dioxane-2-one, 4-methyl-1,3-dioxane-2-one, 4,6-dimethyl-1,3-dioxane-2-one and 1,3-dioxepane-2-one, and polyvalent alkylene carbonate compounds, such as ethylene glycol bis(4-methylene-1,3-dioxolane-2-one)ether, (iv) mono-, di- and polyoxazolidinone compounds, and (v) oxetane compounds and polyvalent oxetane compounds, such as 3-methyl-3-oxetane methanol, 3-butyl-3-oxetane methanol, 3-methyl-3-oxetane ethanol, 3-ethyl-3-oxetane ethanol, 3-butyl-3-oxetane ethanol, 3-chloromethyl-3-methyloxetane and 3-chloromethyl-3-ethyloxetane.

Among these dehydration reactive crosslinking agents, it is preferable to use one or more of the polyhydric alcohol, the alkylene carbonate, the oxazolidinone compound and the (polyvalent) oxetane compound, and it is especially preferable to use at least the polyhydric alcohol.

In addition to these dehydration reactive crosslinking agents, examples of the organic crosslinking agent are (i) epoxy compounds, such as ethylene glycol diglycidyl ether, polyethylene glycol diglycidyl ether, glycerol polyglycidyl ether, diglycerol polyglycidyl ether, polyglycerol polyglycidyl ether, polyethylene diglycidyl ether, propylene glycol diglycidyl ether, polypropylene glycol diglycidyl ether, glycidol and γ-glycidoxypropyltrimethoxysilane, (ii) polyvalent isocyanate compounds, such as 2,4-tolylene diisocyanate and hexamethylene diisocyanate, (iii) polyvalent oxazoline compounds, such as 1,2-ethylenebis oxazoline, (iv) silane coupling agents, such as γ-glycidoxypropyltrimethoxysilane and γ-aminopropyltrimethoxysilane, and (v) polyvalent aziridine compounds, such as 2,2-bishydroxymethylbutanol-tris[3-(1-aziridinyl)propionate]. These crosslinking agents are generally ring-opening reactive crosslinking agents.

These organic crosslinking agents may be used alone or in combination of two or more thereof. Among these, the polyhydric alcohol is preferable because it is highly safe and can improve the hydrophilic property of the surface of the water-absorbing resin particle.

The amount of the organic crosslinking agent used is preferably in a range from 0.001 mass part to 10 mass parts with respect to 100 mass parts of the water-absorbing resin particles, and especially preferably in a range from 0.01 mass part to 5 mass parts. When the amount of the organic crosslinking agent used is less than 0.001 mass part, it is difficult to obtain a desired improvement effect of the absorption property. Meanwhile, when the amount of the organic crosslinking agent used is more than 10 mass parts, it is not economical, miscibility deteriorates (for example, agglomerates are formed), and the desired improvement effect of the absorption property cannot be obtained, which are not preferable.

Water may be used when mixing the organic crosslinking agent and the water-absorbing resin particles. The amount of the water used is preferably in a range from 0.5 mass part to 10 mass parts with respect to 100 mass parts of the water-absorbing resin particles, and more preferably in a range from 0.5 mass part to 5 mass parts. When the amount of the water used is less than 0.5 mass part, it is difficult to obtain the improvement effect of the absorption property, which is not preferable. Meanwhile, when the amount of the water used is more than 10 mass parts, the miscibility deteriorates (for example, agglomerates are formed), which is not preferable.

When mixing the organic crosslinking agent or its aqueous solution, a hydrophilic organic solvent or a third material can be used as a mixing auxiliary agent.

Examples of the hydrophilic organic solvent are (i) lower alcohols, such as methyl alcohol, ethyl alcohol, n-propyl alcohol, isopropyl alcohol, n-butyl alcohol, isobutyl alcohol and t-butyl alcohol, (ii) ketones, such as acetone, (iii) ethers, such as dioxane, tetrahydrofuran and methoxy (poly)ethylene glycol, (iv) amides, such as ε-caprolactam and N,N-dimethylformamide, and (v) sulfoxides, such as dimethyl sulfoxide.

The amount of the hydrophilic organic solvent used depends on the type, particle size, water content, etc. of the water-absorbing resin, however, is preferably from 0 mass part to 10 mass parts with respect to 100 mass parts of the water-absorbing resin particles, and more preferably in a range from 0.1 mass part to 5 mass parts. Moreover, inorganic acid, organic acid, polyamino acid, etc. disclosed in European Patent No. 0668080, surfactant disclosed in WO2005/075070, and/or the like may exist as the third material.

The mixing auxiliary agent may act as the surface crosslinking agent, and it is preferable that the mixing auxiliary agent do not deteriorate the water-absorbing performance of the water-absorbing resin after the surface crosslinking. Volatile alcohol (lower alcohols) having a boiling point of 40° C. or higher but lower than 150° C. is especially desirable because it volatilizes during the surface crosslinking process and residual materials do not remain.

The timing of the surface-crosslinking step is not especially limited as long as it is after the end of the polymerizing step. The surface-crosslinking step may be carried out before the start of the drying step or after the end of the drying step. Preferably, the surface-crosslinking step is carried out after the drying step. Further, it is especially preferable to carry out the surface crosslinking with respect to the water-absorbing resin having the solid content (defined by a weight reduction at 180° C. for 3 hours) of 90% or higher.

(2. Using Peroxide and Organic Crosslinking Agent Together)

In the present invention, the peroxide is mixed with the reaction system in or after the polymerizing step. The peroxide mixed carries out a surface crosslinking reaction of the water-absorbing resin together with the above organic crosslinking agent. The type of the peroxide is not especially limited. Examples of the peroxide are hydrogen peroxides; persulfates, such as sodium persulfate, potassium persulfate and ammonium persulfate; permanganates; inorganic peroxides, such as perchlorate; organic peroxides, such as cumene hydroperoxide, t-butyl hydroperoxide, di-t-butyl peroxide, benzoyl peroxide and lauroyl peroxide. These peroxides may be used alone or in combination of two or more thereof.

Among these, inorganic peroxides, especially persulfate, are preferable since they are highly reactive and highly safe. For example, the ammonium persulfate is used as a food additive in Japan. The amount of the peroxide used is in a range from 0.001 mass part to 3 mass parts with respect to 100 mass parts of the water-absorbing resin particles, preferably in a range from 0.01 mass part to 1 mass part, and especially preferably in a range from 0.01 mass part to 0.5 mass part. When the amount of the peroxide used is less than 0.001 mass part, desired effects (improvement of the liquid permeability and reduction in the amount of residual monomers) cannot be obtained, which is not preferable. Meanwhile, when the amount of the peroxide used is more than 1 mass part, the physical properties deteriorates (for example, the water-absorbing resin deteriorates, water soluble elements increases, etc.), which is not preferable.

The weight ratio of the organic crosslinking agent and the peroxide used in the surface-crosslinking step is preferably from 1:0.005 (organic crosslinking agent:peroxide) to 1:1, more preferably from 1:0.01 to 1:0.8, further preferably from 1:0.03 to 1:0.5, and especially preferably from 1:0.05 to 1:0.3. When the amount of the peroxide used is larger than the amount of the organic crosslinking agent used, the particulate water-absorbing agent deteriorates, and the physical properties may deteriorate (for example, the water-soluble element may increase). Moreover, the particulate water-absorbing agent may become brown or yellow in color. Therefore, this water-absorbing agent may not be suitable for the hygiene material whose amount of the particulate water-absorbing agent is large.

Water may be used when mixing the peroxide and the water-absorbing resin particles. The amount of the water used is preferably in a range from 0.5 mass part to 10 mass parts with respect to 100 mass parts of the water-absorbing resin particles, and more preferably in a range from 0.5 mass part to 5 mass parts. When the amount of the water used is less than 0.5 mass part, it is difficult to uniformly mix the water with the entire water-absorbing resin particles, which is not preferable. Meanwhile, when the amount of the water used is more than 10 mass parts, the miscibility deteriorates (for example, agglomerates are formed), which is not preferable.

The timing of adding the peroxide may be in the polymerizing step or in any step after the polymerizing step, but is not especially limited as long as both the peroxide and the organic crosslinking agent exist in the surface-crosslinking step. As described in the explanation of the polymerizing step, some of the peroxides are used as the polymerization initiator (for example, sodium persulfate). Moreover, the peroxide can also function as the surface crosslinking agent.

Therefore, if there is the peroxide which is added in the polymerizing step, is not used for the polymerization reaction, and remains in the reaction-system, the peroxide carries out the crosslinking reaction in the surface-crosslinking step together with the organic crosslinking agent. Thus, the peroxide may be added only in the polymerizing step.

Moreover, the peroxide may be added in the polymerizing step or anytime after the polymerizing step, such as after the end of the polymerizing step but before the start of the drying step, during the drying step, after the end of the drying step, during, before and after the pulverizing step, during, before and after the classifying step, during, before and after agglomeration, during a transporting step, during an intermediate storing step (hopper, etc.), and during the surface-crosslinking step. If both the peroxide and the organic crosslinking agent can exist in the surface-crosslinking step, the peroxide causes the crosslinking reaction together with the organic crosslinking agent. Therefore, the gel strength improves. On this account, it is possible to improve the liquid diffusibility and liquid permeability of the particulate water-absorbing agent, and also possible to reduce the amount of residual monomers.

An especially preferable timing of adding peroxide is after the end of the drying step that is in or after the polymerizing step. Especially many residual monomers exist in the vicinity of the surface of the dried particulate water-absorbing resin. Therefore, by adding the peroxide to the reaction system after the end of the drying step, it is possible to carry out the reaction of the peroxide and the residual monomer efficiently. Therefore, it is believed that by mixing the peroxide with the reaction system after the end of the drying step, it may be possible to obtain a better effect of reducing the residual monomers.

If water exists in the surface-crosslinking step, it becomes easy to carry out the mixing of the peroxide and the water-absorbing resin, and the mixing of the surface crosslinking agent and the water-absorbing resin. As a result, the surface crosslinking reaction using both the peroxide and the surface crosslinking agent is carried out surely, which is preferable. The amount of the water used is described above.

Thus, if both the peroxide and the organic crosslinking agent can exist in the surface-crosslinking step, it is possible to obtain effects of the present invention. In a manufacturing method of the present invention, it is especially preferable that an aqueous solution containing the peroxide and the organic crosslinking agent be added to the water-absorbing resin particles in the surface-crosslinking step.

In this case, since the aqueous solution containing the peroxide and the organic crosslinking agent is added to the water-absorbing resin particles, the peroxide and the organic crosslinking agent simultaneously act as the surface crosslinking agent. Note that "the surface crosslinking agent" is a material which can carry out the surface crosslinking. As above, if the peroxide and the organic crosslinking agent coexist in the surface-crosslinking step, it is possible to realize the improvement of the liquid permeability, the reduction in the amount of residual monomers, etc. Therefore, the timing of adding the peroxide and the timing of adding the organic crosslinking agent do not have to be identical to each other. However, by adding to the water-absorbing resin the aqueous solution containing the peroxide and the organic crosslinking agent in the surface-crosslinking step, it is possible to obtain especially good effects.

Usually, in the surface-crosslinking step, the heat treatment is carried out after the water-absorbing resin and the surface crosslinking agent are mixed with each other. However, if one of the peroxide and the organic crosslinking agent is added firstly, this firstly added component permeates the water-absorbing resin until when the other component is added. As a result, the percentage of crosslinking in the vicinity of the surface of the obtained water-absorbing resin may decrease.

Meanwhile, in the case of adding the aqueous solution containing the peroxide and the organic crosslinking agent, the crosslinking reaction occurs in the more immediate vicinity of the surface of the water-absorbing resin by these two components. Therefore, it is believed that a surface crosslinking layer which is stronger than the conventional one may be formed, and the gel strength may be improved.

Here, if the surface crosslinking agent is in the form of an aqueous solution and the peroxide contains salt such as persulfate, it is possible to increase the salt concentration of the surface crosslinking agent as compared with a case where only the organic crosslinking agent is used as the surface crosslinking agent. Therefore, it is possible to further suppress permeance of the surface crosslinking agent to the water-absorbing resin particles. On this account, it is believed that the crosslinking by the peroxide and the organic crosslinking agent may be intensively carried out in the more immediate vicinity of the surface of the water-absorbing resin, and the further stronger surface crosslinking layer may be formed.

As a result, it is believed that it may be possible to further improve the liquid diffusibility and liquid permeability of the water-absorbing resin, and also possible to reduce the amount of residual monomers. In this case, it is possible to obtain good effects (shown in Examples) without adding water-soluble polyvalent metal salt (will be described later). On this account, it is possible to say that a method for adding to the water-absorbing resin particles the aqueous solution containing the peroxide and the organic crosslinking agent in the surface-crosslinking step is an especially effective method.

In one embodiment, a manufacturing method of the present invention includes the steps of (i) adding the aqueous solution of the peroxide in or after the polymerizing step but before the surface-crosslinking step, preferably after the drying step, and (ii) adding the aqueous solution of the organic crosslinking agent in the surface-crosslinking step. In this case, the crosslinking by the peroxide occurs inside the particles, too. Therefore, as compared with the method for adding to the water-absorbing resin the aqueous solution containing the peroxide and the organic crosslinking agent in the surface-crosslinking step, the liquid permeability improves, but absorbency against pressure (AAP) slightly deteriorates.

In light of this, it is possible to say that carrying out the crosslinking by the peroxide in the more immediate vicinity of the surface of the water-absorbing resin particle is more effective. Note that "in or after the polymerizing step" includes the polymerizing step, and "before the surface-crosslinking step" does not include the surface-crosslinking step.

Note that it is preferable that the water content of a mixture obtained by adding the aqueous solution of the peroxide after the drying step be 0.5% or more but less than 10%. When the water content is less than 0.5%, it may be impossible to carry out mixing uniformly, which is not preferable. Meanwhile, when the water content is more than 10%, the miscibility and handleability deteriorate (for example, agglomerates are formed), which is not preferable.

Here, the manufacturing method of the present invention may include a heating step that is carried out (i) after the aqueous solution of the peroxide is added after the drying step but (ii) before the surface-crosslinking step is carried out. A heating temperature is not especially defined, but is preferably from 40° C. to 200° C., and more preferably from 50° C. to 150° C. According to this, it is possible to easily disintegrate unwanted agglomerates in the mixture obtained by adding the aqueous solution of the peroxide, and also possible to improve the handleability.

As above, it is preferable that the surface crosslinking reaction be carried out by mixing the water-absorbing resin with the organic crosslinking agent, the peroxide, and the water, and then carrying out the heat treatment. The temperature of the heat treatment depends on the surface crosslinking agent used, but is preferably from 130° C. to 300° C., and more preferably from 150° C. to 250° C. When the temperature of the heat treatment is lower than 130° C., the absorption properties, such as the absorbency against pressure and the liquid permeability, do not improve sufficiently. Meanwhile, when the temperature of the heat treatment is higher than 300° C., the water-absorbing resin particles may deteriorate, and various performances may also deteriorate, so that attentions should be paid to the temperature.

Note that the temperature of the heat treatment is defined by the temperature of a heat medium. However, when the temperature of the heat medium cannot be defined (for example, microwave), the temperature of the heat treatment is defined by the temperature of a material. A heat treatment time is preferably from 1 minute to 2 hours, and more preferably from 5 minutes to an hour.

Moreover, in order to mix the water-absorbing resin particles and the surface crosslinking agent more uniformly, (i) a non-crosslinking water-soluble inorganic base (preferably, alkali metal salt, ammonium salt, alkali metal hydroxide, ammonia or its hydroxide) other than the peroxide, (ii) non-reducing alkali metal salt pH buffering agent (preferably, hydrogencarbonate, dihydrogenphosphate, hydrogenphosphate, or the like), and/or (iii) a surfactant may be used when mixing the water-absorbing resin particles with the surface crosslinking agent. The amount of the above base or agent used depends on the type, particle size, etc. of the water-absorbing resin particle, but is preferably in a range from 0.005 mass part to 10 mass parts with respect to 100 mass parts of the water-absorbing resin particles, and more preferably in a range from 0.05 mass part to 5 mass parts.

A mixing method for mixing the water-absorbing resin particles with the surface crosslinking agent is not especially limited. However, examples of the mixing method are (i) a method for immersing the water-absorbing resin particles in a hydrophilic organic solvent, and mixing, according to need, with the surface crosslinking agent dissolved in water and/or the hydrophilic organic solvent and (ii) a method for spraying or dropping directly onto the water-absorbing resin particles the surface crosslinking agent dissolved in water and/or the hydrophilic organic solvent.

As described in Patent Document 5, the surface crosslinking reaction can be carried out by heating the water-absorbing resin without using the surface crosslinking agent. However, needless to say, the present invention first found that the properties, such as the liquid diffusibility, the liquid permeability, the amount of residual monomers, etc. drastically improve by using both the organic crosslinking agent and the peroxide.

In a manufacturing method of the present invention, it is preferable that the water-soluble polyvalent metal salt be further mixed in or after the polymerizing step. The water-soluble polyvalent metal salt has an effect of improving the liquid permeability of the particulate water-absorbing agent. Taking into account that the particulate water-absorbing agent of the present invention is utilized in the absorber of the hygiene material, such as a diaper, it is preferable that the particulate water-absorbing agent be not colored and less toxic to a human body.

In order to maintain the effects of the water-soluble polyvalent metal salt efficiently for a long time when absorbing liquid, it is preferable to select the water-soluble polyvalent metal salt which can dissolve in room-temperature pure water at a concentration of 5 mass % or more, more preferably at a concentration of 10 mass % or more, and further preferably at a concentration of 20 mass % or more.

Examples of the water-soluble polyvalent metal salt which can be used in the present invention are aluminium chloride, polyaluminium chloride, aluminium sulfate, aluminium nitrate, bis aluminium potassium sulfate, bis aluminium sodium sulfate, potassium alum, ammonium alum, sodium alum, sodium aluminate, calcium chloride, calcium nitrate, magnesium chloride, magnesium sulfate, magnesium nitrate, zinc chloride, zinc sulfate, zinc nitrate, zirconium chloride, zirconium sulphate and zirconium nitrate.

Moreover, in light of the solubility with absorption liquid such as urine, it is preferable to use salt containing the crystal water. More specifically, (i) it is preferable to use aluminuium salt, calcium salt, magnesium salt or zirconium salt, specifically a trivalent compound or a tetravalent compound, and more specifically an aluminium compound such as aluminium chloride, polyaluminium chloride, aluminium sulfate, aluminium nitrate, bis aluminium potassium sulfate, bis aluminium sodium sulfate, potassium alum, ammonium alum, sodium alum or sodium aluminate, (ii) it is especially preferable to use aluminium sulfate, and (iii) it is most preferable to use aluminium sulfate octadecahydrate, or powder of hydrated crystal of aluminium sulfate tetradecahydrate to octadecahydrate, or the like. These may be used alone or in combination of two or more thereof.

In the present invention, it is preferable that the water-soluble polyvalent metal salt be mixed as an aqueous solution with the water-absorbing resin particles. The timing for this mixing may be identical to or different from the timing for adding the organic crosslinking agent and the peroxide. In this case, in order to prevent polyvalent metal ions (for example, aluminium ions) from permeating the water-absorbing resin particles and being diffused in the water-absorbing resin particles, the concentration of the aqueous solution is preferably 50 mass % or higher with respect to the saturated concentration at a use temperature, more preferably 60 mass % or higher, further preferably 70 mass % or higher, further preferably 80 mass % or higher, and especially preferably 90 mass % or higher. As a matter of course, the aqueous solution having the saturated concentration can be used, or slurry of the water-soluble polyvalent metal salt can be used.

The particulate water-absorbing agent obtained by the present invention contains preferably 0.001 mass part to 10 mass parts of the water-soluble polyvalent metal salt with respect to 100 mass parts of the water-absorbing resin that is the main component of the particulate water-absorbing agent, more preferably 0.01 mass part to 5 mass parts, and further preferably 0.1 mass part to 2 mass parts. When the particulate water-absorbing agent obtained by the present invention contains less than 0.001 mass part of the water-soluble polyvalent metal salt, it is impossible to obtain desired improvements of the liquid permeability and block resistance, which is not preferable. Meanwhile, when the particulate water-absorbing agent obtained by the present invention contains more than 10 mass parts of the water-soluble polyvalent metal salt, the absorption properties, such as the CRC and the AAP, may deteriorate.

The particle size and particle size distribution of the water-absorbing resin particle used in the present invention are not especially limited. However, it is preferable to use the water-absorbing resin particle having comparatively small particle size, and the particle size distribution including many small particle size components, since improvements of the water-absorbing performances (the water-absorbing speed, a capillary absorbency, etc.) are significant.

Note that depending on the type and amount of the peroxide, the heat treatment temperature, etc. used in a method for manufacturing the particulate water-absorbing agent of the present invention, the particles may become brown or yellow in color. In such a case, a coloring inhibitor may be used. Examples of the coloring inhibitor are a sulfur-containing reducing agent, amino polyvalent carboxylic acid or its salt, a chelating agent (such as alkyl phosphate or its salt) and hydrogen peroxide.

Examples of the sulfur-containing reducing agent are sodium sulfite, potassium sulfite, calcium sulfite, ammonium sulfite, sulfurous acid, sodium hydrogen sulfite, potassium hydrogen sulfite, ammonium hydrogen sulfite, sodium thiosulfate, potassium thiosulfate, ammonium thiosulfate, magnesium thiosulfate, cysteine and cystine. Especially, sulfite and hydrogen sulfite are preferable.

Moreover, the above chelating agent is preferably a chelating agent having high sequestering ability and chelating ability with respect to Fe and Cu. Specifically, the above chelating agent is a chelating agent having 10 or more of a stability constant with respect to Fe ion, preferably a chelating agent having 20 or more of the stability constant with respect to Fe ion, further preferably amino polyvalent carboxylic acid and its salt, and especially preferably aminocarboxylic acid having three or more carboxyl groups and its salt.

Examples of the polyvalent carboxylic acid are diethylenetriaminepentaacetic acid, triethylenetetraaminehexaacetic acid, cyclohexane-1,2-diaminetetraacetic acid, N-hydroxyethylethylene diamine triacetic acid, ethylene glycol diethyl ether diaminetetraacetic acid, ethylene diamine tetrapropaacetic acid, N-alkyl-N'-carboxymethylaspartic acid, N-argenyl-N'-carboxymethylaspartic acid, and their alkali metal salts, alkali earth metal salts, ammonium salts and amine salts.

The above salt may be completely neutralized, partially neutralized, or a mixture. Among these, diethylenetriaminepentaacetic acid, triethylenetetraaminehexaacetic acid, and N-hydroxyethylethylene diamine triacetic acid and its salt are most preferable.

Moreover, examples of the alkyl phosphate are ethylidene phosphonic acid, 1-hydroxyethylidene-1,1-diphosphonic acid, aminotrimethylene phosphonic acid, ethylenediaminetetra (methylenephosphonic acid), and diethylenetriaminepenta (methylenephosphonic acid). However, especially preferable examples of the alkyl phosphate are 1-hydroxyethylidene-1,1-diphosphonic acid, ethylenediaminetetra (methylenephosphonic acid), and diethylenetriaminepenta (methylenephosphonic acid). Examples of its salt are alkali metal salts, ammonium salts and amine salts of sodium, potassium, etc.

These coloring inhibitors may be used alone or in combination of two or more thereof. The amount of the coloring inhibitor added is preferably from 0.0001 mass part to 10 mass parts with respect to 100 mass parts of the water-absorbing resin, and more preferably from 0.001 mass part to 5 mass parts. When the amount of the coloring inhibitor added is less than 0.0001 mass part, it is impossible to obtain desired effect of color protection, which is not preferable. Meanwhile, when the amount of the coloring inhibitor added is more than 10 mass parts, the water-absorbing performance deteriorates, which is not preferable.

A method for adding the coloring inhibitor is not especially limited. The coloring inhibitor may be added during the polymerization, may be added to the dried water-absorbing resin, or may be used in the surface-crosslinking step.

<Particle Sizes of Water-Absorbing Resin Particle and Particulate Water-Absorbing Agent>

Regarding the particle sizes of the water-absorbing resin particle and the particulate water-absorbing agent in accordance with the present invention, it is preferable that the mass average particle diameter (D50) be from 200 μm to 600 μm and the logarithm standard deviation (σζ) of the particle size distribution be from 0.20 to 0.55, it is more preferable that the mass average particle diameter be from 250 µm to 500 µm and the logarithm standard deviation of the particle size distribution be from 0.23 to 0.45, and it is further preferable that the mass average particle diameter be from 300 µm to 420 µm and the logarithm standard deviation of the particle size distribution be from 0.25 to 0.35.

In the case of the water-absorbing resin particles and the particulate water-absorbing agent having the above mass average particle diameter and the above logarithm standard deviation of the particle size distribution, their particle size distributions become preferable to improve the absorption properties, such as the liquid permeability.

Moreover, in a manufacturing method of the present invention, one or both of (i) the amount of particles each having the particle diameter of less than 150 µm and (ii) the amount of particles each having the particle diameter of 850 µm or more is preferably from 0 mass % to 5 mass % of the entire water-absorbing resin particles or the entire particulate water-absorbing agent, more preferably from 0 mass % to 3 mass %, and further preferably from 0 mass % to 1 mass %. When the amount of particles each having the particle diameter of less than 150 µm is more than 5 mass %, the liquid permeability deteriorates. Therefore, this is not preferable. When the amount of particles each having the particle diameter of less than 150 µm is 5 mass % or less, the amount of fine powder (that is a factor of deteriorating the absorption property) in the water-absorbing resin particles or the particulate water-absorbing agent is small.

In a manufacturing method of the present invention, by adjusting the water-absorbing resin particles and the particulate water-absorbing agent to have the above particle size distribution, it is possible to obtain the particulate water-absorbing agent having excellent absorption properties, such as the liquid permeability. The water-absorbing resin particles having this particle size distribution can be preferably obtained (i) by pulverizing the water-absorbing resin (particles) obtained by the aqueous polymerization or (ii) by putting the particles through a sieve to control the particle size.

<Physical Properties of Particulate Water-Absorbing Agent>

In the present invention, it is preferable that the particulate water-absorbing agent have the above particle diameter, and have the following SFC, CRC, AAP and residual monomer. Further, the particulate water-absorbing agent has a feature that the amount of residual monomers on the surface thereof is small.

In addition to the conventional problems in that (i) the reduction in the mount of residual monomers leads to an increase in cost, (ii) it is difficult to simultaneously realize both the reduction in the water content and the reduction in the amount of residual monomers, (iii) it is difficult to simultaneously realize both high physical properties (especially, high SFC) and the reduction in the amount of residual monomers, etc., the present inventors has tackled a new task of providing the water-absorbing resin of practical use form whose amount of residual monomers is small.

As a result, it is found that a surface residual monomer ratio that is a new parameter truly expresses the amount of residual monomers in the water-absorbing resin of practical use form in the hygiene materials such as diapers. Moreover, the present inventors found that by (i) controlling the surface residual monomer ratio to be a value in a certain range or less than a certain range, and (ii) using the water-absorbing resin whose physical properties (especially, SFC) (the improvements of these physical properties (especially, SFC) cannot be realized simultaneously with the reduction in the amount of residual monomer) are improved to a certain level or higher, it is possible to obtain the hygiene material which can simultaneously realize both high physical properties and the reduction in the amount of residual monomers. Thus, the present inventors has completed a new particulate water-absorbing agent of the present invention.

That is, the particulate water-absorbing agent of the present invention manufactured by, as one example, a method of the present invention is obtained by surface-crosslinking, in the presence of an organic crosslinking agent which can react with a carboxyl group, water-absorbing resin particles, 70 mole % to 100 mole % of which are, as a repeat unit, monomers that are one or both of acrylic acid and its salt, and this particulate water-absorbing agent that is a new particulate water-absorbing agent satisfies (i) the surface residual monomer ratio calculated by Formula 1 below being more than 0% but not more than 5%, (ii) the saline flow conductivity (SFC) being 40 ($\times 10^{-7} \cdot cm^3 \cdot s \cdot g^{-1}$) or more, and (iii) the water content being less than 5%. This particulate water-absorbing agent is suitably used in the hygiene materials such as diapers, and especially high density diapers. As described above, Formula 1 is as follows.

Surface Residual Monomer Ratio (%)=Amount of Surface Residual Monomers (ppm)/Amount of Residual Monomers (ppm)×100    Formula 1

The following will explain a particulate water-absorbing agent of the present invention.

The particulate water-absorbing agent obtained by the present invention has the absorbency against pressure (AAP) of preferably 20 g/g or more, more preferably 22 g/g or more, further preferably 24 g/g or more, and especially preferably 26 g/g or more. The upper limit is 30 g/g.

The particulate water-absorbing agent obtained by the present invention preferably has the above particle size, and further has the centrifuge retention capacity (CRC) of preferably 10 (g/g) or more, more preferably 20 (g/g) or more, and further preferably 25 (g/g) or more. The upper limit is not especially limited, but is preferably 50 (g/g) or less, more preferably 45 (g/g) or less, and further preferably 40 (g/g) or less. When the particulate water-absorbing agent has the centrifuge retention capacity (CRC) of less than 10 (g/g), the amount of absorption is too small, and such particulate water-absorbing agent is not suitable for use in the hygiene material, such as a diaper. Meanwhile, when the particulate water-absorbing agent has the centrifuge retention capacity (CRC) of more than 50 (g/g), the water-absorbing agent having excellent liquid permeability may not be obtained.

The particulate water-absorbing agent obtained by the present invention has the saline flow conductivity (SFC) of preferably 30 ($\times 10^{-7} \cdot cm^3 \cdot s \cdot g^{-1}$) or more, more preferably 40 ($\times 10^{-7} \cdot cm^3 \cdot s \cdot g^{-1}$) or more, yet more preferably 50 ($\times 10^{-7} \cdot cm^3 \cdot s \cdot g^{-1}$) or more, still more preferably 80 ($\times 10^{-7} \cdot cm^3 \cdot s \cdot g^{-1}$) or more, yet more preferably 100 ($\times 10^{-7} \cdot cm^3 \cdot s \cdot g^{-1}$) or more, still more preferably 120 ($\times 10^{-7} \cdot cm^3 \cdot s \cdot g^{-1}$) or more, and yet more preferably 150 ($\times 10^{-7} \cdot cm^3 \cdot s \cdot g^{-1}$) or more.

The upper limit is not especially limited, but is usually preferably 1,000 ($\times 10^{-7} \cdot cm^3 \cdot s \cdot g^{-1}$) or less, more preferably 500 ($\times 10^{-7} \cdot cm^3 \cdot s \cdot g^{-1}$) or less, and further preferably 300 ($\times 10^{-7} \cdot cm^3 \cdot s \cdot g^{-1}$) or less. When the particulate water-absorbing agent has the saline flow conductivity (SFC) of less than 30 ($\times 10^{-7} \cdot cm^3 \cdot s \cdot g^{-1}$), and the concentration of the water-absorbing resin particles in a core of a diaper is 30 mass % or more, more specifically 50 mass % or more, the absorption speed of urine may become low, and this may cause leakage.

The particulate water-absorbing agent obtained by the present invention has the residual monomer of preferably 0 ppm to 500 ppm, further preferably 0 ppm to 300 ppm, and especially preferably 0 ppm to 200 ppm.

Here, in light of safety, it is preferable that the amount of residual monomers be small. In order to keep the amount of residual monomers to a low level, it is necessary to, for example, increase the amount of the peroxide to be used. However, if the amount of the peroxide used is too large, the particulate water-absorbing agent may deteriorate, and the physical properties may deteriorate (for example, the water-soluble element may increase). Moreover, if the amount of the peroxide used is too large, the particulate water-absorbing agent becomes brown or yellow in color. Therefore, this water-absorbing agent may not be suitable for the hygiene material whose amount of the particulate water-absorbing agent is large.

Thus, if the amount of residual monomers is a low level, that is, from 150 ppm to 300 ppm, the physical properties do not deteriorate. Therefore, this water-absorbing agent can be used preferably.

The particulate water-absorbing agent obtained by the present invention has the water content of preferably 0% or more but less than 5%, more preferably 0% or more but less than 3%, and further preferably 0% or more but less than 2%. When the particulate water-absorbing agent has the water content of 5% or more, the amount of absorption per unit weight of the particulate water-absorbing agent becomes small. Therefore, this particulate water-absorbing agent may be unsuitable for the hygiene material having a high content of the particulate water-absorbing agent.

The particulate water-absorbing agent obtained by the present invention has the surface residual monomer ratio of preferably more than 0% but not more than 5%, more preferably more than 0% but not more than 4.5%, and further preferably more than 0% but not more than 4%. When the particulate water-absorbing agent has the surface residual monomer ratio of more than 5%, the residual monomers easily elute from the surface of the particulate water-absorbing agent when absorbing liquid. Therefore, from a safety standpoint, this particulate water-absorbing agent may be unsuitable for the hygiene material having a high content of the particulate water-absorbing agent.

Moreover, when the surface residual monomer ratio is 0%, the amount of the peroxide to be used is large, it is not economical, the particulate water-absorbing agent deteriorates, and the physical properties deteriorate (for example, the water-soluble element increases). Therefore, it is not preferable that the surface residual monomer ratio be 0%. Moreover, in this case, the particulate water-absorbing agent becomes brown or yellow in color. Therefore, this water-absorbing agent may not be suitable for the hygiene material whose amount of the particulate water-absorbing agent is large.

In the present specification, "the residual monomer" is the amount of unreacted monomers contained in the water-absorbing resin particles or in the particulate water-absorbing agent. "The surface residual monomer ratio" will be explained in Examples below.

<Other Additives>

Moreover, the particulate water-absorbing agent obtained by the present invention may be a particulate water-absorbing agent mixed with an organic acid (salt).

Examples of the organic acid (salt) are anisic acid, benzoic acid, formic acid, valeric acid, citric acid, glyoxylic acid, glycolic acid, glutaric acid, succinic acid, tartaric acid, lactic acid, fumaric acid, propionic acid, 3-hydroxypropionic acid, malonic acid, iminodiacetic acid, malic acid, isethionic acid, adipic acid, oxalic acid, salicylic acid, gluconic acid, sorbic acid, p-oxybenzoic acid, and their alkali metal salts or ammonium salts of sodium, potassium, etc. Among these, preferable examples are glycolic acid, tartaric acid, lactic acid, 3-hydroxypropionic acid, malic acid, salicylic acid, hydroxycarboxylic acid such as gluconic acid, and their alkali metal salts or ammonium salts. These may be used alone or in combination of two or more thereof.

Note that the examples of the organic acid (salt) does not include (i) acrylic acid used as a material of the water-absorbing resin and remaining in the water-absorbing resin in the process of its polymerization, or (ii) other reaction by-products derived from acrylic acid.

By mixing the particulate water-absorbing agent obtained by the present invention with the organic acid (salt), it is possible to suppress permeance of the polyvalent metal ions (for example, aluminium ion) to the particulate water-absorbing agent, and the polyvalent metal ions diffuse uniformly on the particle surface. Therefore, the liquid permeability improves drastically.

Moreover, by using the organic acid (salt), it is possible to solve a conventional problem in that the metal components nonuniformly adhere, in the shape of a plane, to the surface of the particulate water-absorbing agent. Therefore, the metal components can uniformly adhere (localize), in the shape of fine spots, in the entire vicinity of the surface of the particulate water-absorbing agent.

In the present invention, the organic acid (salt) may be directly mixed with the particulate water-absorbing agent. However, it is preferable that the organic acid (salt) be mixed with the particulate water-absorbing agent together with the water-soluble polyvalent metal salt, it is more preferable that an aqueous solution of the organic acid (salt) be mixed with the particulate water-absorbing agent together with an aqueous solution of the water-soluble polyvalent metal salt, and it is especially preferable that an aqueous solution containing the organic acid (salt) and the water-soluble polyvalent metal salt be mixed with the particulate water-absorbing agent. The water-soluble polyvalent metal salt has an effect of improving the liquid permeability of the particulate water-absorbing agent. In order to obtain a homogeneous solution of the water-soluble polyvalent metal salt and the organic acid (salt), it is preferable to use the organic acid salt. As the water-soluble polyvalent metal salt, it is possible to use those described in "2. Using Peroxide and Organic Crosslinking Agent Together".

The particulate water-absorbing agent mixed with the organic acid (salt) contains the organic acid (salt) of preferably 0.1 ppm to 10 mass parts with respect to 100 mass parts of the particulate water-absorbing agent, more preferably 0.0001 mass part to 5 mass parts, especially preferably 0.001 mass part to 1 mass part. When the particulate water-absorbing agent mixed with the organic acid (salt) contains the organic acid (salt) of less than 0.1 ppm, it is impossible to suppress the permeance of the metal component to the particulate water-absorbing agent, and the improvement of the liquid permeability cannot be obtained, which are not preferable. Meanwhile, when the particulate water-absorbing agent mixed with the organic acid (salt) contains the organic acid (salt) of more than 10 mass parts, the absorption properties, such as the CRC and the AAP, may deteriorate.

Moreover, the organic acid (salt) and the water-soluble polyvalent metal salt may be used simultaneously in the above-described surface-crosslinking step. However, it is especially preferable to add the organic acid (salt) and the water-soluble polyvalent metal salt to the surface-crosslinked particulate water-absorbing agent (i) in the case of using the water-soluble polyvalent metal salt having corrosivity with respect to various steel products at high temperature, or (ii) in light of easiness of the permeance of the water-soluble polyvalent metal salt to the water-absorbing resin.

In the case of mixing the particulate water-absorbing agent with the organic acid (salt) and the water-soluble polyvalent metal salt, it is preferable to further mix the hydrophilic organic solvent. More preferably, the aqueous solution containing the organic acid (salt) and the water-soluble polyvalent metal salt further contains the hydrophilic organic solvent. By using the hydrophilic organic solvent, it is possible to further uniformly mix the water-soluble polyvalent metal salt with the particulate water-absorbing agent.

Examples of the hydrophilic organic solvent are the hydrophilic organic solvents which can be used in the above-described surface crosslinking treatment.

<Mixer>

In a manufacturing method of the present invention, the peroxide, the organic crosslinking agent, water, polyvalent metal salt, the hydrophilic organic solvent, etc. are added to the reaction system, and then these are mixed by a mixer. Examples of the mixer are a cylindrical mixer, a screw mixer, a screw extruder, a turbulizer, a nauta mixer, a V type mixer, a ribbon mixer, a twin-arm kneader, a fluidized mixer, an air flow mixer, a rotating disc mixer, a roll mixer, a rolling mixer, a Lödige mixer, etc.

As a mixing method, it is possible to adopt batch mixing, continuous mixing, or a combination thereof. However, in light of the industrial production, the continuous mixing is more preferably. The number of rotations when mixing is not especially limited. However, the number of rotations is preferably such that the water-absorbing resin is not damaged. Specifically, the number of rotations is preferably in a range from 1 rpm to 3,000 rpm, more preferably in a range from 2 rpm to 500 rpm, and further preferably in a range from 5 rpm to 300 rpm. When the number of rotations is more than 3,000 rpm, the water-absorbing resin becomes powdery, and the water-absorbing property deteriorates, which are not preferable. Meanwhile, when the number of rotations is less than 1 rpm, the miscibility is insufficient, and the desired improvement effects of the liquid permeability and block resistance cannot be obtained.

<Absorbent Core>

By combining the particulate water-absorbing agent obtained by the present invention with an appropriate material, it is possible to obtain an absorbent core which can be preferably used as, for example, an absorbing layer of a hygiene material. The following will explain the absorbent core.

The absorbent core is a shaped composition (i) which absorbs blood, body fluid, urine, etc., (ii) which is used in hygiene materials, such as paper diapers, sanitary napkins, incontinence pads and medical pads, and (iii) which is made of the particulate water-absorbing agent and other material(s). One example of the material used is cellulose fiber. Specific examples of the cellulose fiber are (i) wood pulp fibers, such as mechanical pulp, chemical pulp, semi-chemical pulp and dissolving pulp which are made of wood, and (ii) artificial cellulose fibers, such as rayon and acetate. Preferable cellulose fiber is the wood pulp fiber. The cellulose fiber may partially contain synthesized fiber, such as nylon or polyester.

In the case of using the particulate water-absorbing agent, obtained by the present invention, as part of the absorbent core, the amount of the particulate water-absorbing agent, obtained by the present invention, in the absorbent core is preferably from 20 mass % to 100 mass %, more preferably from 40 mass % to 100 mass %, further preferably from 50 mass % to 100 mass %, and yet further preferably from 70 mass % to 100 mass %. When this amount is less than 20 mass %, a sufficient effect may not be obtained.

In order to obtain the absorbent core using the particulate water-absorbing agent obtained by the present invention and the cellulose fiber, it is possible to accordingly select a known method for obtaining the absorbent core, such as (i) a method for dispersing the water-absorbing agent on papers or mats made of the cellulose fiber and, according to need, sandwiching the agent with the papers or the mats, or (ii) a method for uniformly blending the cellulose fiber and the particulate water-absorbing agent.

A preferable method is to dry-blend the particulate water-absorbing agent and the cellulose fiber and then to compress the resulting mixture. This method can prevent the water-absorbing agent from dropping off from the cellulose fiber significantly. It is preferable to carry out this compression under heat. In this case, the temperature range is, for example, from 50° C. to 200° C. Moreover, in order to obtain the absorbent core, methods disclosed in Tokuhyohei 9-509591 (Published Japanese Translation of PCT International Publication for Patent Application 9-509591) and Tokukaihei 9-290000 (Japanese Unexamined Patent Publication No. 290000/1997) can be used preferably.

The particulate water-absorbing agent obtained by the present invention has excellent liquid diffusibility and liquid permeability, and the amount of residual monomers contained in the particulate water-absorbing agent obtained by the present invention is small. Therefore, by using this particulate water-absorbing agent, it is possible to obtain the absorbent core which has excellent water-absorbing properties and is highly safe.

Since the particulate water-absorbing agent obtained by the present invention has an excellent water-absorbing property, it can be used in various applications as a water-absorbing/water-holding agent. For example, the particulate water-absorbing agent obtained by the present invention can be used as (i) a water-absorbing/water-holding agent for an absorbing product, such as a paper diaper, a sanitary napkin, an incontinence pad or a medical pad, (ii) a water-holding agent for agriculture or horticulture, such as a bog moss substitution, a soil modifier/conditioner, a water-holding agent and an agent for maintaining effects of agricultural chemicals, (iii) a water-holding agent for architecture, such as an agent for preventing dew drops on interior wall materials and a cement additive, (iv) a release control agent, (v) a cold insulator, (vi) a disposal body warmer, (vii) a sludge coagulant, (viii) a freshness keeping agent for foods, (ix) an ion-exchange column material, (x) a dehydrating agent for sludge or oil, (xi) a drying agent, (xii) a humidity control material, etc. Moreover, the particulate water-absorbing agent obtained by the present invention is especially preferably used in the hygiene material for absorbing feces, urine, or blood, such as the paper diaper and the sanitary napkin.

The particulate water-absorbing agent obtained by the present invention has excellent liquid diffusibility and liquid permeability, and the amount of residual monomers contained in the particulate water-absorbing agent is small. Therefore, the particulate water-absorbing agent obtained by the present invention is especially preferable for manufacturing a thin absorbent hygiene material. That is, in the case of manufacturing a thin absorbent hygiene material, conventionally used is a method for reducing the amount of the hydrophilic fiber and increasing the amount of the water-absorbing resin so as to increase the concentration of the water-absorbing resin in the hygiene material. However, this causes a problem that is an influence on a skin (skin disorder) due to the residual monomers, etc. contained in the water-absorbing resin. By using the particulate water-absorbing agent obtained by the present invention, it is possible to obtain a thin absorbent hygiene material which has high water-absorbing property and is highly safe.

In the case of using the absorbent core in a hygiene material, such as the paper diaper, the sanitary napkin, the incontinence pad or the medical pad, the hygiene material preferably includes (a) a liquid permeable top sheet which is provided so as to lie next to a body of a wearer, (b) a liquid impermeable back sheet which is provided far from the body of the wearer but next to the clothes of the wearer, and (c) the absorbent core provided between the top sheet and the back sheet. The absorbent core may include two or more layers, or may be used together with a pulp layer, etc.

The present invention is not limited to the description of the embodiments above, but may be altered by a skilled person within the scope of the claims. An embodiment based on a proper combination of technical means disclosed in different embodiments is encompassed in the technical scope of the present invention.

EXAMPLES

The following will explain the present invention in detail using Examples. However, the present invention is not limited to these Examples. In the following description, for the sake of convenience, "mass part(s)" may be referred to as "part(s)", and "liter(s)" may be referred to as "L". Moreover, "mass %" may be referred to as "wt %".

Performances of the water-absorbing resin particle and the particulate water-absorbing agent were measured by the following methods. Unless otherwise specified, the following measurements were carried out at room temperature (20 to 25° C.) and 50% RH.

In the case of the water-absorbing resin composition having been used as an end product, such as the hygiene material, the water-absorbing resin composition was wet. Therefore, the measurement was carried out after the water-absorbing resin composition which was separated from the end product was dried under reduced pressure at a low temperature (for example, dried for 12 hours under the reduced pressure of 1 mmHg or less at 60° C.). Moreover, the water content of the water-absorbing resin composition used in Examples and Comparative Examples of the present invention was 8 mass % or less.

<Centrifuge Retention Capacity (CRC)>

The centrifuge retention capacity (CRC) indicates absorbency measured under no pressure for 30 minutes using a 0.90 mass % saline solution (physiological saline solution). Note that the CRC may also be referred to as "absorbency under no pressure".

0.200 g of the water-absorbing resin particles or the particulate water-absorbing agent was uniformly put into a bag (85 mm×60 mm) made of nonwoven fabric (produced by Nangoku Pulp Kogyo Co., Ltd., Product Name: Heatron Paper, Type: GSP-22), and the bag was heat sealed and immersed in a large excess (usually about 500 ml) of the 0.90 mass % saline solution (sodium chloride aqueous solution) at room temperature. The bag was pulled out of the solution 30 minutes later, was drained off using a centrifuge (produced by Kokusan Co., Ltd., Centrifuge: Type H-122) by centrifugal force (250 G) described in "edana ABSORBENCY II 441.1-99" for 3 minutes. Then, a weight W1 (g) of the bag was measured. Moreover, the same operation was carried out without the water-absorbing resin particles or the water-absorbing resin composition. Then, a weight W0 (g) of the bag was measured. Then, the centrifuge retention capacity (CRC) (g/g) was calculated by the following formula using W1 and W0.

Centrifuge Retention Capacity (CRC) (g/g)=($W1$(g)−$W0$(g))/(Weight (g) of Water-absorbing Resin Particle or Water-absorbing Agent)−1

<Absorbency Against Pressure (AAP)>

The absorbency against pressure (AAP) indicates absorbency measured under pressure of 4.83 kPa for 60 minutes using the 0.90 mass % saline solution. Note that the AAP may also be referred to as "absorbency under pressure of 4.83 kPa".

An apparatus shown in FIG. 1 was used. A stainless steel 400 mesh metal screen 101 (mesh size 38 µm) was fusion-bonded to the bottom of a plastic supporting cylinder 100 having an internal diameter of 60 mm, and 0.900 g of the water-absorbing resin particles or the particulate water-absorbing agent 102 was evenly spread on the metal screen 101 at room temperature (20 to 25° C.) and 50% RH. Then, a piston 103 and a load 104 were placed in this order on the water-absorbing resin particles or the particulate water-absorbing agent 102. The piston 103 and the load 104 were adjusted so as to apply load of 4.83 kPa (0.7 psi) uniformly to the water-absorbing resin particles or the particulate water-absorbing agent 102. Each of the piston 103 and the load 104 has an external diameter which is slightly smaller than 60 mm so that (i) there is no gap between the piston 103 (the load 104) and the supporting cylinder 100 and (ii) the vertical motions of the piston 103 (the load 104) were smooth. A weight Wa (g) of this complete set of measuring device was measured.

A glass filter 106 (produced by Sogo Rikagaku Glass Works Co., Ltd., Pore Diameter: 100 µm to 120 µm) having a diameter of 90 mm was placed inside a petri dish 105 having a diameter of 150 mm, and a 0.90 mass % saline solution 108 (20° C. to 25° C.) was added to the petri dish 105 so that the liquid level of the 0.90 mass % saline solution 108 is the same as the top surface of the glass filter 106. Then, a piece of filter paper 107 (produced by Advantec Toyo Co., Ltd., Product Name: (JIS P 3801, No. 2), Thickness: 0.26 mm, Retained Particle Diameter: 5 µm) having a diameter of 90 mm was placed on the glass filter 106 so that the surface of the filter paper 107 got wet entirely, and excessive liquid was removed.

The complete set of measuring device was placed on the wet filter paper, and the liquid was absorbed under pressure. The complete set of measuring device was lifted up an hour later, and a weight Wb (g) of the complete set of measuring device was measured. Then, the absorbency against pressure (AAP) (g/g) was calculated by the following formula using Wa and Wb.

Absorbency Against Pressure (AAP)=($Wb$(g)−$Wa$(g))/(Weight (0.900 g) of Water-absorbing Resin Particle or Water-absorbing Agent)

<Saline Flow Conductivity (SFC)>

The saline flow conductivity (SFC) indicates liquid permeability of swollen water-absorbing resin particles or swollen particulate water-absorbing agent. The larger the SFC value is, the higher the liquid permeability is.

The measurement was carried out in accordance with a saline flow conductivity (SFC) test disclosed in Tokuhyohei 9-509591 (Published Japanese Translation of PCT International Publication for Patent Application 9-509591).

Figure 2:
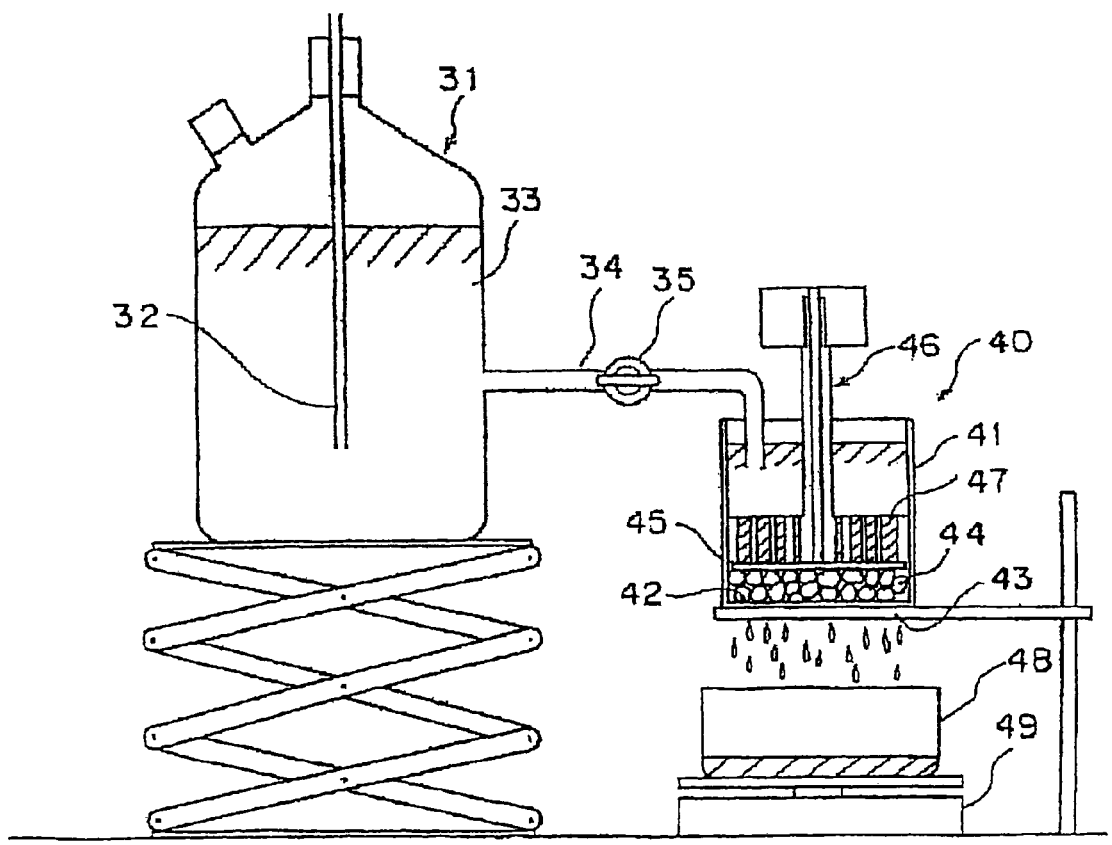
FIG. 2 is a schematic diagram showing an apparatus for measuring the SFC.

An apparatus shown in FIG. 2 was used. The water-absorbing resin particles or the particulate water-absorbing agent (0.900 g) evenly spread in a container 40 was swollen in artificial urine (1) under pressure of 0.3 psi (2.07 kPa) for 60 minutes, and then the height of a gel layer of a gel 44 was recorded. Next, under pressure of 0.3 psi (2.07 kPa), a 0.69 mass % saline solution 33 was supplied from a tank 31 at a certain hydrostatic pressure so as to pass through the swollen gel layer. This SFC test was carried out at room temperature (20° C. to 25° C.). Using a computer and a balance, the amount of liquid passing through the gel layer was recorded every 20 seconds for 10 minutes as a function of time.

A flow speed Fs (T) of the liquid passing through (mainly between the particles of) the swollen gel 44 was determined by dividing an increased weight (g) by an increased time (s) and expressed by g/s. A time the hydrostatic pressure became constant and the flow speed became stable is Ts. Data obtained in 10 minutes from Ts is used for calculating the flow speed. Then, the value of Fs (T=0), that is, an initial flow speed of the liquid passing through the gel layer was calculated using the flow speed. Fs (T=0) was extrapolated from a result of a least square method of Fs (T) versus time.

$$\text{Saline Flow Conductivity}(SFC) = (Fs(t=0) \times L0)/(\rho \times A \times \Delta P)$$
$$= (Fs(t=0) \times L0)/139506$$

In this formula, Fs (t=0) denotes the flow speed and is shown by g/s, L0 denotes the height of the gel layer and is shown by cm, $\rho$ denotes the density of a NaCl solution (1.003 g/cm$^3$), A denotes the area of an upper surface of the gel layer in a cell 41 (28.27 cm$^2$), and $\Delta P$ denotes the hydrostatic pressure applied to the gel layer (4,920 dyne/cm$^2$). In addition, the unit of the SFC value is $10^{-7} \cdot cm^3 \cdot s \cdot g^{-1}$.

Regarding the apparatus shown in FIG. 2, a glass tube 32 was inserted into a tank 31, the lower end of the glass tube 32 was placed so that the liquid level of the 0.69 mass % saline solution 33 was maintained to be 5 cm above the bottom of the swollen gel 44 in the cell 41. The 0.69 mass % saline solution 33 in the tank 31 was supplied to the cell 41 through an L-shaped tube 34 having a cock 35. A container 48 for collecting the liquid having passed through the cell 41 was placed under the cell 41, and this collecting container 48 was placed on an even balance 49. The internal diameter of the cell 41 was 6 cm, and a No. 400 stainless steel metal screen 42 (mesh size 38 gm) was provided at the bottom of the cell 41. A hole 47 through which liquid can pass was formed at a lower portion of the piston 46, and a glass filter 45 having high permeability was provided at a bottom of the piston 46 so that the water-absorbing resin particles, the water-absorbing agent, or the swollen gel do not get into the hole 47. The cell 41 was placed on a base for mounting a cell, and a stainless steel metal screen 43 which does not disturb the penetration of the liquid was placed on a surface of the base, the surface being in contact with the cell 41.

Artificial urine (1) was a mixture of 0.25 g of calcium chloride dihydrate, 2.0 g of potassium chloride, 0.50 g of magnesium chloride hexahydrate, 2.0 g of sodium sulfate, 0.85 g of ammonium dihydrogen phosphate, 0.15 g of diammonium hydrogen phosphate, and 994.25 g of pure water.

<Mass Average Particle Diameter (D50) and Logarithm Standard Deviation ($\sigma\zeta$) of Particle Size Distribution>

The water-absorbing resin particles or the particulate water-absorbing agent were sieved by JIS standard sieves having mesh sizes of 850 μm, 710 μm, 600 μm, 500 μm, 300 μm, 150 μm, 45 μm etc., and a residual percentage R was plotted to a logarithmic probability sheet. Note that a sieve(s) may be added according to need. Thus, a particle diameter corresponding to R=50 mass % was considered as the mass average particle diameter (D50). Moreover, the logarithm standard deviation ($\sigma\zeta$) of the particle size distribution is shown by the following formula. The smaller the value of $\sigma\zeta$ is, the narrower the particle size distribution is.

$$\sigma\zeta = 0.5 \times \ln(X2/X1)$$

In this formula, X1 denotes the particle diameter when R=84.1%, and X2 denotes the particle diameter when R=15.9%

A classification method used when measuring the mass average particle diameter (D50) and the logarithm standard deviation ($\sigma\zeta$) of the particle size distribution was as follows. 10.0 g of the water-absorbing resin particles or the particulate water-absorbing agent was put into the JIS standard sieve (THE IIDA TESTING SIEVE: Diameter of 8 cm) having the mesh size of 850 μm, 710 μm, 600 μm, 500 μm, 300 μm, 150 μm, or 45 μm at room temperature (20° C. to 25° C.) and 50% RH, and classified with a sieve shaker (IIDA SIEVE SHAKER, TYPE: ES-65, SER. No. 0501) for 5 minutes.

<Amount of Water Soluble Element (Water Soluble Component)>

184.3 g of the 0.90 mass % saline solution was measured and poured in a lidded plastic container having a capacity of 250 ml, 1.00 g of the water-absorbing resin particles or the particulate water-absorbing agent was added to this solution, and this mixture was stirred with a stirrer for 16 hours. Thus, the soluble element in the resin was extracted. This extraction liquid was filtered by a piece of filter paper (produced by Advantec Toyo Co., Ltd., Product name: (JIS P 3801, No. 2), Thickness: 0.26 mm, Retained Particle Diameter: 5 μm), and 50.0 g of filtrate was obtained as a measurement solution.

First, only the 0.90 mass % saline solution was titrated with a 0.1N NaOH aqueous solution to pH10, and then was titrated with a 0.1N HCl aqueous solution to pH2.7. Thus, blank titer ([bNaOH] ml, [bHCl] ml) was obtained.

Similar titration was carried out with respect to the measurement solution. Thus, titer ([NaOH] ml, [HCl] ml) was obtained.

For example, in the case of the water-absorbing resin particles or the particulate water-absorbing agent containing known amounts of acrylic acid and its sodium salt, the amount of the soluble element in the water-absorbing resin particles or in the particulate water-absorbing agent can be calculated by the following formula using the average molecular weight of the monomer and the titer obtained by the above-described titration. When the amount of acrylic acid and its sodium salt was unknown, the average molecular weight of the monomer was calculated using a neutralization ratio obtained by the titration.

Amount of Soluble Element (mass %)=0.1×(Average Molecular Weight)×184.3×100×([HCl]−[bHCl])/ 1,000/1.0/50.0

Neutralization Ratio (mol %)=(1−([NaOH]− [bNaOH])/([HCl]−[bHCl]))×100

<Amount of Residual Monomers (ppm)>

1.00 g of the water-absorbing resin particles or the particulate water-absorbing agent was dispersed in 184.3 g of the 0.90 mass % saline solution, and was stirred by a magnetic stirrer and a stirring bar having a length of 25 mm for 16 hours (at a rotating speed of 400 rpm to 500 rpm). Thus, the residual monomers were extracted. Then, the swollen gel was filtered by a piece of filter paper (produced by Toyo Roshi Kaisha, Ltd., No. 2, Retained Particle Diameter defined by JIS P 3801: 5 μm), and this filtrate was further filtered by a HPLC sample pretreatment filter (chromato disk 25A produced by Kurabo Industries, Ltd., Water type, Pore size: 0.45 μm). Thus, a residual monomer measurement sample was obtained.

The residual monomer measurement sample was analyzed by a high-performance liquid chromatography (HPLC). In consideration of (i) an external standard that is a calibration curve obtained by analyzing a monomer standard solution having a known concentration and (ii) the dilution degree of the water-absorbing resin particles or the particulate water-absorbing agent with respect to the 0.90 mass % saline solution, the amount of residual monomers of the water-absorbing resin particles or the particulate water-absorbing agent was quantitated. Measurement conditions of the HPLC were as follows.

Carrier liquid: Phosphoric acid aqueous solution obtained by diluting 3 ml of phosphoric acid (85 mass %, produced by Wako Pure Chemical Industries, Ltd., Special Grade Chemical) with 1,000 ml of super pure water (Specific Resistance: 15 MΩ·cm or more)

Carrier speed: 0.7 ml/min.

Column: SHODEX RSpak DM-614 (produced by Showa Denko K.K.)

Column temperature: 23±2° C.

Wavelength: UV205 nm

<Paint Shaker Test>

A paint shaker test (PS) includes the steps of (i) putting 10 g of glass beads each having a diameter of 6 mm and 30 g of the water-absorbing resin particles or the particulate water-absorbing agent in a glass container having a diameter of 6 cm and a height of 11 cm, (ii) attaching the glass container to a paint shaker (produced by Toyo Seiki Seisakusho, Product No. 488), and (iii) shaking the glass container at 800 cycle/min (CPM). Details of this apparatus is disclosed in Tokukaihei 9-235378 (Japanese Unexamined Patent Publication 9-235378).

A paint shaker test including a step of shaking for 30 minutes is referred to as "Paint Shaker Test 1", and a paint shaker test including a step of shaking for 10 minutes is referred to as "Paint Shaker Test 2".

After shaking the glass container, the glass beads were removed by using the JIS standard sieve having a mesh size of 2 mm, and the damaged water-absorbing resin particles or the damaged particulate water-absorbing agent were obtained.

<Water Content>

1.00 g of the water-absorbing resin particles or the particulate water-absorbing agent was put in an aluminium cup whose bottom surface has a diameter of about 50 mm, and a total weight $W_2$ (g) of the water-absorbing resin particles or the particulate water-absorbing agent, and the aluminium cup was measured. Then, the aluminium cup was placed in an oven of ambient temperature of 180° C. for 3 hours, so as to be dried. 3 hours later, the water-absorbing resin particles or the particulate water-absorbing agent and the aluminium cup were taken out of the oven, and those were sufficiently cooled down to room temperature by a desiccator. After that, a total weight $W_3$ (g) of the dried water-absorbing resin particles or the dried particulate water-absorbing agent, and the aluminium cup was measured. The water content was calculated by the following formula.

Water Content (mass %)=$(W_2-W_3)$/(Mass (g) of Water-absorbing Resin Particles or Particulate Water-absorbing Agent)×100

<Surface Residual Monomer Ratio (SRMR)>

In a vial with a screw cap (produced by Maruemu Corporation, No. 7 (external diameter of 35 mm×height of 78 mm×opening inner diameter of 20 mm)), 1.00 g of the particulate water-absorbing agent was dispersed in 10.0 g of a mixed solvent of methanol (for use in high-performance liquid chromatography, produced by Kishida Chemical Co., Ltd.)/2N hydrochloric acid=97.5/2.5, and this mixture was stirred by a magnetic stirrer and a stirring bar having a length of 25 mm for an hour (at a rotating speed of 250 rpm). Thus, the residual monomers on the surfaces of the particles were extracted.

After that, supernatant fluid was filtered by a HPLC sample pretreatment filter (chromato disk 25A produced by Kurabo Industries, Ltd., Water type, Pore size: 0.45 μm). Thus, filtrate was obtained. This filtrate was diluted 2 fold with the carrier liquid (phosphoric acid aqueous solution obtained by diluting 3 ml of phosphoric acid (85 mass %, produced by Wako Pure Chemical Industries, Ltd., Special Grade Chemical) with 1,000 ml of super pure water (Specific Resistance: 15 MΩ·cm or more)). Thus, a surface residual monomer ratio measurement sample was obtained.

This surface residual monomer ratio measurement sample was analyzed by the high-performance liquid chromatography (HPLC) (see <Amount of Residual Monomers (ppm)> for the measurement conditions of the HPLC). Next, the obtained numerical value was commuted in consideration of (i) the external standard that is the calibration curve obtained in <Amount of Residual Monomers (ppm)> and (ii) the difference between the dilution degree of the particulate water-absorbing agent with respect to a methanol/2N hydrochloric acid mixed solvent and the dilution degree of the particulate water-absorbing agent with respect to the carrier liquid. Thus, the amount of surface residual monomers of the particulate water-absorbing agent was obtained. The surface residual monomer ratio was calculated by the following formula.

Surface Residual Monomer Ratio (%)=Amount of Surface Residual Monomers (ppm)/Amount of Residual Monomers (ppm)×100

<Absorbency with Respect to Surface-Crosslinking Agent (SCRC)>

Absorbency with respect to the surface-crosslinking agent (SCRC) indicates absorbency measured under no pressure for 5 minutes using various surface-crosslinking agent aqueous solutions used in a step of surface-crosslinking the water-absorbing resin particle not subjected to the surface-crosslinking.

0.100 g of the water-absorbing resin particles was uniformly put into a bag (85 mm×60 mm) made of nonwoven fabric (produced by Nangoku Pulp Kogyo Co., Ltd., Product Name: Heatron Paper, Type: GSP-22), and the bag was heat sealed and immersed in the surface-crosslinking agent aqueous solution (usually about 100 ml).

The bag was pulled out of the solution 5 minutes later, was drained off using a centrifuge (produced by Kokusan Co., Ltd., Centrifuge: Type H-122) by centrifugal force (250 G) described in "edana ABSORBENCY II 441.1-99" for 3 minutes. Then, a weight $W_4$ (g) of the bag was measured. Moreover, the same operation was carried out without the water-absorbing resin particles. Then, a weight $W_5$ of the bag was measured. Then, the absorbency with respect to the surface-crosslinking agent (SCRC) (g/g) was calculated by the following formula using $W_4$ and $W_5$.

Absorbency With Respect To Surface-crosslinking Agent (SCRC) (g/g)=$(W_4$ (g)$-W_5$ (g))/(Mass (g) of Water-absorbing Resin Particles)−1

The smaller the absorbency with respect to the surface-crosslinking agent (SCRC) is, the more (i) the permeance of the surface-crosslinking agent aqueous solution to the water-absorbing resin particle is suppressed, (ii) the miscibility improves, and (iii) the formation of agglomerates is suppressed.

Manufacture Example 1

In a reactor made by lidding a jacketed stainless steel twin-arm kneader having two sigma blades and a capacity of 10 liters, 436.4 g of acrylic acid, 4,617.9 g of a 37 mass % sodium acrylate aqueous solution, 381.0 g of pure water and 11.40 g of polyethylene glycol diacrylate (molecular weight 523) were dissolved. Thus, reaction liquid was prepared.

Next, this reaction liquid was degassed for 20 minutes with nitrogen gas. Then, 29.07 g of a 10 mass % sodium persulfate aqueous solution and 24.22 g of a 0.1 mass % L-ascorbic acid aqueous solution were added to the reaction liquid while stirring. About one minute later, polymerization started.

Then, the polymerization was carried out at 20° C. to 95° C. while the generated gel was being pulverized. Hydrated gel crosslinked polymer was taken out 30 minutes after the polymerization started. The obtained hydrated gel crosslinked polymer was fragmented so that the diameter of each fragmented piece was about 5 mm or less.

These fragmented pieces of the hydrated gel crosslinked polymer were spread out on a 50 mesh metal screen, and were dried by hot air of 180° C. for 50 minutes. The dried pieces were pulverized with a roll mill, and the pulverized pieces were further classified by JIS standard sieves having the mesh sizes of 850 μm and 150 μm. Thus, obtained were water-absorbing resin particles (A) having the mass average particle diameter of 372 μm and indeterminate pulverized shapes. The centrifuge retention capacity (CRC) of the water-absorbing resin particle (A) was 32.3 g/g, and the water soluble element of the water-absorbing resin particle (A) was 10.0 mass %.

Example 1

100 mass parts of the water-absorbing resin particles (A) obtained in Manufacture Example 1 was uniformly mixed with a surface crosslinking agent that was a liquid mixture of 0.4 mass part of 1,4-butanediol, 0.6 mass part of propylene glycol, 0.1 mass part of sodium persulfate and 2.7 mass parts of pure water. Then, the resulting mixture was subjected to a heat treatment of 200° C. for 30 minutes. Further, the particles were disintegrated so that the disintegrated particles can pass through the JIS standard sieve having a mesh size of 850 μm. Next, Paint Shaker Test 1 was carried out using the particles. Thus, a particulate water-absorbing agent (1) whose surface was crosslinked was obtained.

Example 2

A particulate water-absorbing agent (2) was obtained in the same manner as Example 1 except that the heat treatment time was 40 minutes.

Example 3

A particulate water-absorbing agent (3) was obtained in the same manner as Example 1 except that the amount of sodium persulfate was 0.2 mass part.

Example 4

1 mass part of a 27 mass % solution of liquid aluminium sulfate for tap water (produced by Asahi Chemical Industry Co., Ltd.) was mixed with 0.17 mass part of a 60% sodium lactate aqueous solution (produced by Purac Japan K.K.). Thus, a clear homogeneous solution was obtained.

100 mass parts of the particulate water-absorbing agent (1) was uniformly mixed with 1.0 mass part of this solution, and the resulting mixture was dried at 60° C. for an hour. The dried agent was disintegrated so that the disintegrated particles can pass through the JIS standard sieve having the mesh size of 850 μm. Next, Paint Shaker Test 2 was carried out using the particles. Thus, a particulate water-absorbing agent (A) was obtained.

Example 5

A particulate water-absorbing agent (B) was obtained in the same manner as Example 4 except that the particulate water-absorbing agent (2) was used.

Example 6

A particulate water-absorbing agent (C) was obtained in the same manner as Example 4 except that the particulate water-absorbing agent (3) was used.

Comparative Example 1

In Comparative Examples 1 and 2, the surface crosslinking was carried out without using peroxide.

100 mass parts of the water-absorbing resin particles (A) obtained in Manufacture Example 1 was uniformly mixed with a surface crosslinking agent that was a liquid mixture of 0.4 mass part of 1,4-butanediol, 0.6 mass part of propylene glycol and 2.7 mass parts of pure water. Then, the resulting mixture was subjected to a heat treatment of 200° C. for 30 minutes. Further, the particles were disintegrated so that the disintegrated particles can pass through the JIS standard sieve having the mesh size of 850 μm. Next, Paint Shaker Test 1 was carried out using the particles. Thus, a comparative particulate water-absorbing agent (1) whose surface was crosslinked was obtained.

Comparative Example 2

A comparative particulate water-absorbing agent (2) was obtained in the same manner as Comparative Example 1 except that the heat treatment time was 40 minutes.

Manufacture Example 2

While stirring a solution (A) by a magnetic stirrer in a polypropylene container, a solution (B) was poured at one stretch in an open system in order to mix the solutions (A) and (B). Note that (i) the polypropylene container was covered with styrene foam that was a heat insulator, and had an internal diameter of 80 mm and a capacity of 1 liter, (ii) the solution (A) was a mixture of 185.4 g of acrylic acid, 0.942 g of polyethylene glycol diacrylate (molecular weight 523) (0.07 mole % with respect to the acrylic acid) and 1.13 g of a 1.0 mass % diethylenetriaminepentaacetic acid pentasodium aqueous solution, and (iii) the solution (B) was a mixture of 148.53 g of a 48.5 mass % sodium hydroxide aqueous solution and 159.71 g of ion-exchange water whose temperature was adjusted to 50° C. Obtained was a monomer aqueous solution whose temperature was increased to about 100° C. due to the heat of neutralization and the heat of dissolution.

4.29 g of a 3 mass % sodium persulfate aqueous solution was added to the obtained monomer aqueous solution, and this mixture was stirred for several seconds. Then, the mixture was poured in an open system into a stainless steel vat-type container (i) whose surface temperature was increased to 100° C. by a hotplate (NEO HOTPLATE H1-1000, produced by Iuchi Seiei Do K.K.), (ii) to an inner surface of which Teflon (registered trademark) was attached, and (iii) whose bottom surface was 250 mm×250 mm. The stainless steel vat-type container had a bottom surface of 250 mm×250 mm, an upper surface of 640 mm×640 mm and a height of 50 mm. A central cross section of the stainless steel vat-type container was a trapezoid, and the upper surface was open.

A polymerization started soon after the monomer aqueous solution was poured into the vat. The polymerization proceeded while the solution generated water vapor and was expanded and foamed laterally and vertically. Finally, the resultant shrank and its size became a bit larger than the bottom surface. This expansion and shrinkage ended within about 1 minute. After keeping the resultant in the container for 4 minutes, hydrated gel crosslinked polymer was taken out.

The obtained hydrated gel crosslinked polymer was pulverized with a meat chopper (ROYAL MEAT CHOPPER VR400K, produced by Iizuka Kogyo, K.K.) having a dice diameter of 9.5 mm. Thus, fragmented pieces of the hydrated gel crosslinked polymer were obtained.

These fragmented pieces of the hydrated gel crosslinked polymer were spread out on a 50 mesh metal screen, and were dried by hot air of 180° C. for 50 minutes. The dried pieces of the hydrated gel crosslinked polymer were pulverized with a roll mill, and were classified with the JIS standard sieves having mesh sizes of 710 μm and 150 μm. As a result, obtained was water-absorbing resin particles (B) having the mass average particle diameter of 350 μm and indeterminate pulverized shapes. The centrifuge retention capacity (CRC) of the water-absorbing resin particle (B) was 34.0 g/g, and the water soluble element of the water-absorbing resin particle (B) was 11.0 mass %.

Example 7

100 mass parts of the water-absorbing resin particles (B) obtained in Manufacture Example 2 was uniformly mixed with a surface crosslinking agent that was a liquid mixture of 0.3 mass part of 1,4-butanediol, 0.6 mass part of propylene glycol, 0.1 mass part of sodium persulfate and 3.0 mass parts of pure water. Then, the resulting mixture was subjected to a heat treatment of 200° C. for 30 minutes. Further, the particles were disintegrated so that the disintegrated particles can pass through the JIS standard sieve having the mesh size of 850 μm. Next, Paint Shaker Test 1 was carried out using the particles. Thus, a particulate water-absorbing agent (4) whose surface was crosslinked was obtained.

Example 8

A particulate water-absorbing agent (D) was obtained in the same manner as Example 4 except that the particulate water-absorbing agent (4) was used.

Comparative Example 3

100 mass parts of the water-absorbing resin particles (B) obtained in Manufacture Example 2 was uniformly mixed with a surface crosslinking agent that was a liquid mixture of 0.3 mass part of 1,4-butanediol, 0.6 mass part of propylene glycol and 3.0 mass parts of pure water. Then, the resulting mixture was subjected to a heat treatment of 200° C. for 30 minutes. Further, the particles were disintegrated so that the disintegrated particles can pass through the JIS standard sieve having the mesh size of 850 μm. Next, Paint Shaker Test 1 was carried out using the particles. Thus, a comparative particulate water-absorbing agent (3) whose surface was crosslinked was obtained.

Comparative Example 4

A comparative particulate water-absorbing agent (A) was obtained in the same manner as Example 4 except that the comparative particulate water-absorbing agent (1) was used.

Comparative Example 5

A comparative particulate water-absorbing agent (B) was obtained in the same manner as Example 4 except that the comparative particulate water-absorbing agent (2) was used.

Comparative Example 6

A comparative particulate water-absorbing agent (C) was obtained in the same manner as Example 4 except that the comparative particulate water-absorbing agent (3) was used.

Example 9

100 mass parts of the water-absorbing resin particles (B) obtained in Manufacture Example 2 was uniformly mixed with a surface treatment agent that was a liquid mixture of 0.3 mass part of 1,4-butanediol, 0.6 mass part of propylene glycol, 0.3 mass part of ammonium persulfate and 3.0 mass parts of pure water. Then, the resulting mixture was subjected to a heat treatment of 200° C. for 50 minutes. Further, the particles were disintegrated so that the disintegrated particles can pass through the JIS standard sieve having the mesh size of 850 μm. Next, Paint Shaker Test 1 was carried out using the particles. Thus, a particulate water-absorbing agent (5) whose surface was crosslinked was obtained.

Example 10

A particulate water-absorbing agent (E) was obtained in the same manner as Example 4 except that the particulate water-absorbing agent (5) was used.

Comparative Example 7

100 mass parts of the water-absorbing resin particles (A) obtained in Manufacture Example 1 was uniformly mixed with a treatment agent that was a liquid mixture of 0.2 mass part of sodium persulfate and 2.7 mass parts of pure water. Then, the resulting mixture was subjected to a heat treatment of 200° C. for 40 minutes. Further, the particles were disintegrated so that the disintegrated particles can pass through the JIS standard sieve having the mesh size of 850 μm. Next, Paint Shaker Test 1 was carried out using the particles. Thus, a comparative particulate water-absorbing agent (4) whose surface was crosslinked was obtained.

Comparative Example 8

A comparative particulate water-absorbing agent (D) was obtained in the same manner as Example 4 except that the comparative particulate water-absorbing agent (4) was used.

Comparative Example 9

100 mass parts of the water-absorbing resin particles (A) obtained in Manufacture Example 1 was uniformly mixed with a surface crosslinking agent that was a liquid mixture of 0.4 mass part of 1,4-butanediol, 0.6 mass part of propylene glycol, 0.1 mass part of sodium sulfate and 2.7 mass parts of pure water. Then, the resulting mixture was subjected to a heat treatment of 200° C. for 40 minutes. Further, the particles were disintegrated so that the disintegrated particles can pass through the JIS standard sieve having the mesh size of 850 μm. Next, Paint Shaker Test 1 was carried out using the particles. Thus, a comparative particulate water-absorbing agent (5) whose surface was crosslinked was obtained.

Comparative Example 10

A comparative particulate water-absorbing agent (E) was obtained in the same manner as Example 4 except that the comparative particulate water-absorbing agent (5) was used.

Example 11

100 mass parts of the water-absorbing resin particles (A) obtained in Manufacture Example 1 was mixed with 3.0 mass parts of a 3.3% sodium persulfate aqueous solution, and the resulting mixture was dried at 60° C. for an hour. The obtained dried particles were disintegrated so that the disintegrated particles can pass through the JIS standard sieve having the mesh size of 850 μm. Thus, a water-absorbing resin particles (C) was obtained. Next, 100 mass parts of the obtained water-absorbing resin particles (C) was uniformly mixed with a surface crosslinking agent that was a liquid mixture of 0.4 mass part of 1,4-butanediol, 0.6 mass part of propylene glycol and 2.7 mass parts of pure water. Then, the resulting mixture was subjected to a heat treatment of 200° C. for 30 minutes. Further, the particles were disintegrated so that the disintegrated particles can pass through the JIS standard sieve having the mesh size of 850 μm. Next, Paint Shaker Test 1 was carried out using the particles. Thus, a particulate water-absorbing agent (6) whose surface was crosslinked was obtained.

Example 12

A particulate water-absorbing agent (F) was obtained in the same manner as Example 4 except that the particulate water-absorbing agent (6) was used.

Manufacture Example 3

Water-absorbing resin particles (D) having the mass average particle diameter of 340 μm and indeterminate pulverized shapes were obtained in the same manner as Manufacture Example 2 except that the JIS standard sieves having the mesh sizes of 710 μm and 45 μm were used to control the particle size. The centrifuge retention capacity (CRC) of the water-absorbing resin particle (D) was 33.0 g/g, and the water soluble element of the water-absorbing resin particle (D) was 12.5 mass %.

Comparative Example 11

A comparative particulate water-absorbing agent (F) was obtained in the same manner as Examples 7 and 8 except that the water-absorbing resin particles (D) obtained in Manufacture Example 3 were used.

Comparative Example 12

100 mass parts of the water-absorbing resin particles (A) obtained in Manufacture Example 1 was uniformly mixed with 3.0 mass parts of water. Then, the resulting mixture was dried at 60° C. for an hour. The dried particles were disintegrated so that the disintegrated particles can pass through the JIS standard sieve having the mesh size of 850 μm. Thus, water-absorbing resin particles (E) were obtained. Next, 100 mass parts of the obtained water-absorbing resin particles (E) was uniformly mixed with a surface crosslinking agent that was a liquid mixture of 0.4 mass part of 1,4-butanediol, 0.6 mass part of propylene glycol and 2.7 mass parts of pure water. Then, the resulting mixture was subjected to a heat treatment of 200° C. for 30 minutes. Further, the particles were disintegrated so that the disintegrated particles can pass through the JIS standard sieve having the mesh size of 850 μm. Next, Paint Shaker Test 1 was carried out using the particles. Thus, a comparative particulate water-absorbing agent (6) whose surface was crosslinked was obtained.

Comparative Example 13

A comparative particulate water-absorbing agent (G) was obtained in the same manner as Example 4 except that the comparative particulate water-absorbing agent (6) was used.

Comparative Example 14

A comparative particulate water-absorbing agent (7) was obtained in the same manner as Example 1 except that (i) the heat treatment is not carried out, and (ii) while stirring the mixture in a separable flask of quartz, the mixture is irradiated with an ultraviolet ray at an irradiation intensity of 60 W/cm² for 10 minutes at room temperature by using an ultraviolet light irradiation apparatus (produced by Ushio Inc., UV-152/1MNSC3-AA06) to which a metal halide lamp (produced by Ushio Inc., UVL-1500M2-N1) is attached.

Tables 1 and 2 show measurement results of the centrifuge retention capacity (CRC), the absorbency against pressure (AAP), the saline flow conductivity (SFC), the residual monomer (RM), the surface residual monomer ratio (SRMR) and the water content of each of the particulate water-absorbing agents (1) to (6), the particulate water-absorbing agents (A) to (F), the comparative particulate water-absorbing agents (1) to (7) and the comparative particulate water-absorbing agents (A) to (G) obtained in Examples and Comparative Examples. Table 1 shows the results obtained by using the peroxide during the surface crosslinking, and Table 2 shows the results obtained by adding the peroxide to the water-absorbing resin before the surface crosslinking.

Moreover, Table 3 shows measurement results of the particle size distribution, and Table 4 shows measurement results of the absorbency with respect to the surface crosslinking agent (SCRC). Note that in Table 1, the organic crosslinking agent "BD" is short for "1,4-butanediol", and the organic crosslinking agent "PG" is short for "propylene glycol". Moreover, in Tables 1 and 2, "RM" is short for "Residual Monomer", and "SRMR" is short for "Surface Residual Monomer Ratio". In Table 3, for example, "on 710 μm" shows the percentage (weight %) of particles remaining on the JIS standard sieve having the mesh size of 710 μm, and "thru. 45 μm" shows the percentage (weight %) of particles having passed through the JIS standard sieve having the mesh size of 45 μm.

TABLE 1

| | Used water-absorbing resin particle | Organic cross-linking agent | Peroxide Type | Amount (wt %) | Other additive | CRC (g/g) | AAP (g/g) | SFC ($10^{-7} \cdot cm^3 \cdot s \cdot g^{-1}$) | RM (ppm) | SRMR (%) | Water content (%) |
|---|---|---|---|---|---|---|---|---|---|---|---|
| Example 1 | Particulate water-absorbing agent (1) | (A) | BD, PG | Sodium persulfate | 0.1 | — | 28.9 | 26.0 | 70 | 225 | 4.5 | 1.4 |
| Example 2 | Particulate water-absorbing agent (2) | (A) | BD, PG | Sodium persulfate | 0.1 | — | 27.0 | 24.5 | 88 | — | — | — |
| Example 3 | Particulate water-absorbing agent (3) | (A) | BD, PG | Sodium persulfate | 0.2 | — | 29.0 | 25.3 | 65 | — | — | — |
| Example 4 | Particulate water-absorbing agent (A) | (A) | BD, PG | Sodium persulfate | 0.1 | Aluminum sulfate/ sodium lactate | 29.2 | 24.3 | 137 | 220 | 4.6 | 1.6 |
| Example 5 | Particulate water-absorbing agent (B) | (A) | BD, PG | Sodium persulfate | 0.1 | Aluminum sulfate/ sodium lactate | 27.0 | 23.2 | 152 | — | — | — |
| Example 6 | Particulate water-absorbing agent (C) | (A) | BD, PG | Sodium persulfate | 0.2 | Aluminum sulfate/ sodium lactate | 29.1 | 24.3 | 115 | 180 | 3.7 | 1.4 |
| Example 7 | Particulate water-absorbing agent (4) | (B) | BD, PG | Sodium persulfate | 0.1 | — | 27.3 | 24.8 | 68 | — | — | — |
| Example 8 | Particulate water-absorbing agent (D) | (B) | BD, PG | Sodium persulfate | 0.1 | Aluminum sulfate/ sodium lactate | 27.2 | 23.9 | 118 | 260 | 4.3 | 1.5 |
| Example 9 | Particulate water-absorbing agent (5) | (B) | BD, PG | Ammonium persulfate | 0.3 | — | 27.5 | 24.5 | 73 | — | — | — |
| Example 10 | Particulate water-absorbing agent (E) | (B) | BD, PG | Ammonium persulfate | 0.3 | Aluminum sulfate/ sodium lactate | 27.4 | 24.1 | 127 | — | — | — |
| Comparative Example 1 | Comparative particulate water-absorbing agent (1) | (A) | BD, PG | — | — | — | 28.9 | 25.6 | 55 | — | — | — |
| Comparative Example 2 | Comparative particulate water-absorbing agent (2) | (A) | BD, PG | — | — | — | 27.2 | 24.4 | 61 | — | — | — |
| Comparative Example 3 | Comparative particulate water-absorbing agent (3) | (B) | BD, PG | — | — | — | 27.3 | 24.9 | 46 | — | — | — |
| Comparative Example 4 | Comparative particulate water-absorbing agent (A) | (A) | BD, PG | — | — | Aluminum sulfate/ sodium lactate | 29.0 | 23.8 | 98 | 320 | 9.6 | 1.5 |
| Comparative Example 5 | Comparative particulate water-absorbing agent (B) | (A) | BD, PG | — | — | Aluminum sulfate/ sodium lactate | 27.5 | 22.5 | 118 | — | — | — |
| Comparative Example 6 | Comparative particulate water-absorbing agent (C) | (B) | BD, PG | — | — | Aluminum sulfate/ sodium lactate | 27.2 | 24.2 | 98 | 350 | 9.8 | 1.4 |
| Comparative Example 7 | Comparative particulate water-absorbing agent (4) | (A) | — | Sodium persulfate | 0.2 | — | 33.0 | 10.1 | 0 | — | — | — |
| Comparative Example 8 | Comparative particulate water-absorbing agent (D) | (A) | — | Sodium persulfate | 0.2 | Aluminum sulfate/ sodium lactate | 32.9 | 9.8 | 1 | — | — | — |
| Comparative Example 9 | Comparative particulate water-absorbing agent (5) | (A) | BD, PG | Sodium sulfate | 0.1 | — | 27.6 | 24.0 | 47 | 340 | 9.3 | 1.3 |

TABLE 1-continued

| | Used water-absorbing resin particle | Organic cross-linking agent | Peroxide Type | Amount (wt %) | Other additive | CRC (g/g) | AAP (g/g) | SFC ($10^{-7} \cdot cm^3 \cdot s \cdot g^{-1}$) | RM (ppm) | SRMR (%) | Water content (%) |
|---|---|---|---|---|---|---|---|---|---|---|---|
| Comparative Example 10 | Comparative particulate water-absorbing agent (E) | (A) | BD, PG | Sodium sulfate | 0.1 | Aluminum sulfate/ sodium lactate | 27.3 | 22.7 | 112 | — | — | — |
| Comparative Example 11 | Comparative particulate water-absorbing agent (F) | (D) | BD, PG | Sodium persulfate | 0.1 | Aluminum sulfate/ sodium lactate | 26.5 | 21.2 | 63 | 325 | 7.8 | 1.4 |
| Comparative Example 14 | Comparative particulate water-absorbing agent (7) | (A) | BD, PG | Sodium persulfate | 0.1 | — | 31.2 | 9.5 | 0 | — | — | 7.3 |

TABLE 2

| | | Additive | Added amount (wt %) | CRC (g/g) | AAP (g/g) | SFC ($10^{-7} \cdot cm^3 \cdot s \cdot g^{-1}$) | RM (ppm) | SRMR (%) | Water content (%) |
|---|---|---|---|---|---|---|---|---|---|
| Example 11 | Particulate water-absorbing agent (6) | 3.3% sodium persulfate | 3.0 | 27.3 | 24.0 | 95 | — | — | — |
| Comparative Example 12 | Comparative particulate water-absorbing agent (6) | Pure water | 3.0 | 27.2 | 24.5 | 83 | — | — | — |
| Example 12 | Particulate water-absorbing agent (F) | 3.3% sodium persulfate | 3.0 | 27.1 | 24.2 | 156 | 250 | 4.8 | 1.8 |
| Comparative Example 13 | Comparative particulate water-absorbing agent (G) | Pure water | 3.0 | 27 | 24.3 | 135 | 315 | 9.3 | 2 |

TABLE 3

| | D50 (µm) | σζ | on 710 µm | on 600 µm | on 500 µm | on 300 µm | on 150 µm | on 45 µm | thru. 45 µm |
|---|---|---|---|---|---|---|---|---|---|
| Particulate water-absorbing agent (A) | 380 | 0.33 | 0.2 | 3.5 | 16.2 | 56.7 | 22.2 | 1 | 0.1 |
| Particulate water-absorbing agent (D) | 355 | 0.27 | 0 | 1.5 | 7.4 | 65.8 | 24.9 | 0.4 | 0 |
| Particulate water-absorbing agent (F) | 388 | 0.31 | 0.5 | 4.1 | 16.4 | 58.6 | 19.8 | 0.6 | 0 |
| Comparative particulate water-absorbing agent (A) | 377 | 0.35 | 0.4 | 4.2 | 16.8 | 52.5 | 25 | 0.9 | 0.1 |
| Comparative particulate water-absorbing agent (C) | 359 | 0.26 | 0 | 1.7 | 7.7 | 66.8 | 23.5 | 0.3 | 0 |
| Comparative particulate water-absorbing agent (F) | 336 | 0.56 | 0 | 3.3 | 8.6 | 51.1 | 21.7 | 13.8 | 1.5 |
| Comparative particulate water-absorbing agent (G) | 395 | 0.33 | 0.4 | 5.1 | 19.2 | 53.9 | 20.3 | 1 | 0.1 |

TABLE 4

| | Used water-absorbing resin particle | Organic crosslinking agent | Sodium persulfate (wt %) | Water (wt %) | SCRC (g/g) |
|---|---|---|---|---|---|
| Example 1 | (A) | BD, PG | 0.1 | 2.7 | 10.5 |
| Example 3 | (A) | BD, PG | 0.2 | 2.7 | 8.4 |
| Example 7 | (B) | BD, PG | 0.1 | 3.0 | 12.1 |
| Comparative Example 1 | (A) | BD, PG | — | 2.7 | 98.2 |
| Comparative Example 3 | (B) | BD, PG | — | 3.0 | 110.0 |

The results shown in Tables 1 and 2 indicate that the particulate water-absorbing agent obtained by the present invention has excellent liquid permeability. Moreover, the results shown in Tables 1 and 2 indicate that by using the peroxide, the residual monomers and the surface residual monomer ratio (SRMR) are drastically reduced in addition to the improvement of the liquid permeability. Therefore, the present invention can easily provide the particulate water-absorbing agent which has excellent liquid permeability, is highly safe, and shows excellent performance when used in the paper diaper, etc.

Moreover, the results shown in Table 4 indicate that by using the organic crosslinking agent and sodium persulfate together, the absorbency of the water-absorbing resin particle with respect to the surface-crosslinking agent aqueous solution (SCRC) decreases drastically. This indicates that using the organic crosslinking agent and sodium persulfate together is effective to improve the miscibility of the surface-crosslinking agent to the water-absorbing resin and to suppress the formation of agglomerates.

In the method for manufacturing the particulate water-absorbing agent of the present invention, the reaction system can be mixed with the peroxide after the drying step that is in or after the polymerizing step. Especially many residual monomers exist in the vicinity of the surface of the dried particulate water-absorbing resin. Therefore, it is believed that by mixing the reaction system with the peroxide after the drying step, the reaction between the peroxide and the residual monomers can be carried out efficiently. As a result, it is believed that it may be possible to obtain higher effect of reducing the residual monomers.

Moreover, in the method for manufacturing the particulate water-absorbing agent of the present invention, it is preferable that the surface-crosslinking step be carried out in the presence of the peroxide, the organic crosslinking agent and the water. According to the above, by using the water, the peroxide and the water-absorbing resin particles are mixed with each other smoothly, and the surface crosslinking agent and the water-absorbing resin particles are also mixed with each other smoothly. As a result, it is believed that the surface crosslinking reaction using the peroxide and the surface crosslinking agent may be carried out surely. As a result, it is believed that it may be possible to further surely improve the liquid diffusibility and the liquid permeability of the particulate water-absorbing agent, and reduce the amount of residual monomers.

Moreover, in the surface-crosslinking step of the method for manufacturing the particulate water-absorbing agent of the present invention, it is preferable that an aqueous solution containing the peroxide and the organic crosslinking agent be added to the reaction system. According to the above, the aqueous solution containing the peroxide and the organic crosslinking agent is used as the surface crosslinking agent, and the peroxide and the organic crosslinking agent simultaneously act as the surface crosslinking agent. Therefore, it is believed that a surface crosslinking layer stronger than a conventional one may be formed and the gel strength may be improved. Inorganic peroxide is preferably used as the peroxide.

Moreover, especially in the case of using, as the peroxide, peroxide having salt, such as persulfate, the salt concentration of the surface crosslinking agent can be increased as compared with a case of using only the organic crosslinking agent as the surface crosslinking agent. Therefore, it is possible to suppress the permeance of the surface crosslinking agent to the water-absorbing resin particle. Therefore, this is preferable because it is believed that (i) the crosslinking by the peroxide and the organic crosslinking agent may be intensively carried out in the more immediate vicinity of the surface of the water-absorbing resin, and (ii) a further stronger surface crosslinking layer may be formed.

Moreover, since the permeance of the surface-crosslinking agent to the water-absorbing resin is suppressed, the surface-crosslinking agent spreads more uniformly to respective particles. This may brings about an effect of improving the physical properties. Moreover, from a standpoint of manufacturing, using this surface-crosslinking agent may bring about effects of (i) improving the miscibility of the surface-crosslinking agent to the water-absorbing resin and (ii) suppressing the formation of agglomerates which are usually formed during the heat treatment in the surface-crosslinking step.

Note that the above "agglomerate" is an aggregate of particles and is formed by heating the water-absorbing resin which contains a large amount of the surface-crosslinking agent locally. The agglomerate is usually formed when the miscibility of the surface-crosslinking agent to the water-absorbing resin is insufficient. When the heat treatment is carried out in a state in which the agglomerates are formed, the heat does not reach the surfaces of the particles inside these agglomerates, so that the crosslinking reaction does not progress sufficiently. Therefore, if this agglomerate breaks down in the subsequent manufacturing steps such as "during transportation", this results in the water-absorbing resin containing particles which are not crosslinked sufficiently. Therefore, it is believed that the agglomerate causes the deterioration of the physical properties.

Moreover, since peroxide radical generated by heating the peroxide reacts with the residual monomers in the water-absorbing resin, the amount of residual monomers can be reduced. As above, since especially many residual monomers exist in the vicinity of the surface of the dried particulate water-absorbing resin, it is believed that by using the peroxide and the organic crosslinking agent in the surface-crosslinking step, it may be possible to obtain the highest effect of reducing the residual monomers.

As a result, according to the above method, it is believed that it may be possible to improve the liquid diffusibility and liquid permeability of the particulate water-absorbing agent and also possible to reduce the amount of residual monomers.

Moreover, in the method for manufacturing the particulate water-absorbing agent of the present invention, (i) in the polymerizing step or after the polymerizing step but before the surface-crosslinking step, an aqueous solution of the peroxide may be added to the reaction system, and (ii) in the surface-crosslinking step, an aqueous solution of the organic crosslinking agent may be added to the reaction system.

According to the above, the aqueous solution of the peroxide is added before the surface treatment. Therefore, as compared with a method for adding to the reaction system the aqueous solution containing the peroxide and the organic crosslinking agent in the surface-crosslinking step, it is estimated that the degree of crosslinking in the vicinity of the surface of the water-absorbing resin particle decreases, but it is greater than that of a conventional water-absorbing resin particle. As a result, it is believed that it may be possible to improve the liquid diffusibility and liquid permeability of the particulate water-absorbing agent more than those of a conventional water-absorbing agent, and also possible to reduce the amount of residual monomers.

Moreover, it is preferable that a heating temperature in the surface-crosslinking step be from 150° C. to 250° C. According to the above, since the heating temperature is in a preferable range for carrying out the surface crosslinking reaction, it is believed that the surface crosslinking reaction may be carried out efficiently. As a result, it is believed that it may be possible to improve the liquid diffusibility and liquid permeability of the particulate water-absorbing agent, and also possible to reduce the amount of residual monomers more efficiently.

Moreover, it is preferable that the organic crosslinking agent be a dehydration reactive crosslinking agent. Since the dehydration reactive crosslinking agent reacts with the acid group of the water-absorbing resin particle, and can carry out the surface crosslinking by the dehydration reaction, it can be preferably used as the surface crosslinking agent.

It is preferable that the peroxide be persulfate. Since, among peroxides, persulfate is highly reactive and highly safe, it is possible to stably carry out the crosslinking in the more immediate vicinity of the surface of the water-absorbing resin particle. Therefore, persulfate helps achieve an object of the present invention, that is, it helps to provide the particulate water-absorbing agent which is highly functional and highly safe.

It is preferable that the reaction system be further mixed with a water-soluble polyvalent metal salt in or after the polymerizing step. The water-soluble polyvalent metal salt has an effect of improving the liquid permeability of the water-absorbing resin particle. Therefore, it is possible to obtain the particulate water-absorbing agent having further improved liquid permeability.

Moreover, in the method for manufacturing the particulate water-absorbing agent of the present invention, it is preferable that a centrifuge retention capacity (CRC) of the particulate water-absorbing agent with respect to a physiological saline solution be 25 (g/g) or more, and a saline flow conductivity (SFC) of the particulate water-absorbing agent be 40 ($\times 10^{-7} \cdot cm^3 \cdot s \cdot g^{-1}$) or more. According to the manufacturing method of the present invention, it is possible to obtain the particulate water-absorbing agent which has excellent liquid permeability, etc. and is highly safe. However, if the CRC and SFC of the obtained particulate water-absorbing agent are in the above respective range, the particulate water-absorbing agent has excellent liquid permeability. Therefore, it is possible to provide more highly functional particulate water-absorbing agent.

According to the manufacturing method of the present invention, the surface-crosslinking step is carried out using the peroxide and the organic crosslinking agent. Therefore, it is possible to easily provide the particulate water-absorbing agent which has excellent liquid permeability and is highly safe.

Since the particulate water-absorbing agent has an excellent water-absorbing property, etc., it can be used in various applications as a water-absorbing/water-holding agent. For example, the particulate water-absorbing agent can be used as (i) a water-absorbing/water-holding agent for an absorbing product, such as a paper diaper, a sanitary napkin, an incontinence pad and a medical pad, (ii) a water-holding agent for agriculture or horticulture, such as a bog moss substitution, a soil modifier/conditioner, a water-holding agent and an agent for maintaining effects of agricultural chemicals, (iii) a water-holding agent for architecture, such as an agent for preventing dew drops on interior wall materials and a cement additive, (iv) a release control agent, (v) a cold insulator, (vi) a disposal body warmer, (vii) a sludge coagulant, (viii) a freshness keeping agent for foods, (ix) an ion-exchange column material, (x) a dehydrating agent for sludge or oil, (xi) a drying agent, (xii) a humidity control material, etc. Moreover, the particulate water-absorbing agent is especially preferably used in the hygiene material for absorbing feces, urine, or blood, such as the paper diaper and the sanitary napkin.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

What is claimed is:

1. A particulate water-absorbing agent obtained by surface-crosslinking, by an organic crosslinking agent which is able to react with a carboxyl group, water-absorbing resin particles, 70 mole % to 100 mole % of which are, as a repeat unit, monomers selected from acrylic acid and/or its salt, the particulate water-absorbing agent satisfying (i) to (iii) below:

(i) a surface residual monomer ratio calculated by Formula 1 below being more than 0% but not more than 5%;

$$\text{Surface Residual Monomer Ratio (\%)} = \text{Amount of Surface Residual Monomers (ppm)}/\text{Amount of Residual Monomers (ppm)} \times 100 \qquad \text{Formula 1}$$

(ii) a saline flow conductivity (SFC) being 40 ($\times 10^{-7} \cdot cm^3 \cdot s \cdot g^{-1}$) or more; and (iii) a water content being less than 5%.

2. The particulate water-absorbing agent as set forth in claim 1, further satisfying (iv) to (vi) below:

(iv) a mass average particle diameter (D50) being from 250 gm to 500 gm;

(v) a logarithm standard deviation ($\sigma\zeta$) of a particle size distribution being from 0.23 to 0.45; and (vi) a percentage of particles each having a particle diameter of less than 150 µm being 5 mass % or less of the entire particulate water-absorbing agent.

3. The particulate water-absorbing agent as set forth in claim 1, wherein the residual monomers are from 150 ppm to 300 ppm.

4. The particulate water-absorbing agent as set forth in claim 1, wherein the surface crosslinking is carried out by peroxide, the organic crosslinking agent and a water-soluble polyvalent metal salt.

5. The particulate water-absorbing agent as set forth in claim 1, wherein an amount of the organic crosslinking agent is in a range from 0.001 mass part to 10 mass parts with respect to 100 mass parts of the water-absorbing resin particles.

6. The particulate water-absorbing agent as set forth in claim 1, wherein the organic crosslinking agent is a dehydration reactive crosslinking agent.

7. The particulate water-absorbing agent as set forth in claim 1, wherein the organic crosslinking agent is one or more selected from the group consisting of polyhydric alcohol, alkylene carbonate, a oxazolidinone compound, and a (polyvalent) oxetane compound.

8. The particulate water-absorbing agent as set forth in claim 1, wherein a water-soluble polyvalent metal salt is further contained.

9. The particulate water-absorbing agent as set forth in claim 8, wherein the water soluble polyvalent metal salt is in a range from 0.001 mass part to 10 mass parts with respect to 100 mass parts of the water-absorbing resin particles.

10. The particulate water-absorbing agent as set forth in claim 8, wherein a water content of the particulate water-absorbing agent is 0% or more but less than 3%.

11. The particulate water-absorbing agent as set forth in claim 8, wherein the amount of particles each having a particle diameter of 850 µm or more is in a range from 0 mass % to 5 mass % and an amount of particles each having a particle diameter of less than 150 µm is in a range from 0 mass % to 5 mass % with respect to all of the water-absorbing resin particles, a centrifuge retention capacity (CRC) is in a range from 25 (g/g) to 40 (g/g), and an absorbency against pressure (AAP) is in a range from 20 g/g to 30 g/g.

12. The particulate water-absorbing agent as set forth in claim 1, wherein the particulate water-absorbing agent is manufactured by a method comprising the step of surface-crosslinking, in the presence of 0.001 mass part to 10 mass parts of an organic crosslinking agent which is able to react with a carboxyl group, 100 mass parts of water-absorbing resin particles obtained through at least a step of polymerizing an aqueous solution of unstaturated monomers, in the surface crosslinking step, a reaction system of the method being not irradiated with an active energy ray having a wavelength that is equal to or less than a wavelength of an ultraviolet ray, and the surface crosslinking step being carried out in the presence of peroxide, the organic crosslinking agent and water.

13. The particulate water-absorbing agent as set forth in claim 12, wherein in the surface crosslinking step, an aqueous solution containing the peroxide and the organic crosslinking agent is added to the reaction system.

14. The particulate water-absorbing agent as set forth in claim 12, wherein a heating temperature in the surface crosslinking step is from 150° C. to 250° C.

15. The particulate water-absorbing agent as set forth in claim 12, wherein the organic crosslinking agent is a dehydration reactive crosslinking agent.

16. The particulate water-absorbing agent as set forth in claim 12, wherein the peroxide is in a range from 0.001 mass part to 3 mass parts with respect to 100 mass parts of the water-absorbing resin particles.

* * * * *